United States Patent
Mao et al.

(10) Patent No.: US 10,976,309 B2
(45) Date of Patent: *Apr. 13, 2021

(54) METHODS, COMPOSITIONS AND KITS FOR LABELING OF PROTEINS

(71) Applicant: Biotium, Inc., Fremont, CA (US)

(72) Inventors: Fei Mao, Fremont, CA (US); Lori Michelle Roberts, Belmont, CA (US); Chingying Cheung, San Ramon, CA (US)

(73) Assignee: BIOTIUM, INC., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/101,234

(22) Filed: Aug. 10, 2018

(65) Prior Publication Data

US 2019/0277836 A1    Sep. 12, 2019

Related U.S. Application Data

(63) Continuation of application No. 14/030,993, filed on Sep. 18, 2013, now Pat. No. 10,107,799.

(60) Provisional application No. 61/702,729, filed on Sep. 18, 2012.

(51) Int. Cl.
*G01N 33/532* (2006.01)

(52) U.S. Cl.
CPC .................. *G01N 33/532* (2013.01)

(58) Field of Classification Search
CPC .................................................. G01N 33/532
See application file for complete search history.

(56) References Cited

U.S. PATENT DOCUMENTS

| | | | |
|---|---|---|---|
| 6,917,726 B2 | 7/2005 | Levene et al. | |
| 7,013,054 B2 | 3/2006 | Levene et al. | |
| 7,170,050 B2 | 1/2007 | Turner et al. | |
| 7,181,122 B1 | 2/2007 | Levene et al. | |
| 7,267,673 B2 | 9/2007 | Pilcher et al. | |
| 7,292,742 B2 | 11/2007 | Levene et al. | |
| 8,709,830 B2 * | 4/2014 | Mao ..................... | G01N 33/532 436/544 |
| 9,097,667 B2 | 8/2015 | Mao et al. | |
| 1,010,779 A1 | 10/2018 | Mao et al. | |
| 2009/0305410 A1 * | 12/2009 | Mao ....................... | C09B 11/08 435/375 |
| 2018/0143113 A1 * | 5/2018 | Mao ..................... | G01N 33/532 |

OTHER PUBLICATIONS

Amine-Reactive Probes for ab labeling. Invitrogen/Molecular Probes. Mar. 8, 2011.
APEX antibody labeling kits. Life Technologies. Aug. 28, 2012.
DyLight® Amine-Reactive Dyes Instructions. Thermo Scientific. 2011.

(Continued)

*Primary Examiner* — Tracy Vivlemore
*Assistant Examiner* — Nam P Nguyen
(74) *Attorney, Agent, or Firm* — Wilson Sonsini Goodrich & Rosati

(57) ABSTRACT

Provided herein are methods, compositions and kits for labeling of target proteins such as antibodies. The methods, compositions and kits are suited for labeling of such proteins that are mixed with other non-target molecules including BSA, gelatin, and other complex biological molecules.

17 Claims, 10 Drawing Sheets

CF647 Mix-n-Stain labeling of mouse anti-transferrin receptor antibody or isotype control with 10-fold excess of BSA or gelatin, flow cytometry

(56) References Cited

OTHER PUBLICATIONS

Innova Biosciences, "Guide to Antibody Labeling and Detection", pp. 1-9, published Jul. 2010.
Lightning-Link® Rapid Conjugation System. Innova Bioscience. 2011.
Notice of allowance dated Jul. 11, 2018 for U.S. Appl. No. 14/030,993.
Office action dated Mar. 10, 2016 for U.S. Appl. No. 14/030,993.
Office action dated Nov. 18, 2016 for U.S. Appl. No. 14/030,993.
Remove BSA and gelatin from antibody solutions using Melon™ Gel. Tech Tip #55. Thermo Scientific. 2010.
U.S. Appl. No. 14/030,993 Office Action dated Dec. 26, 2017.

\* cited by examiner

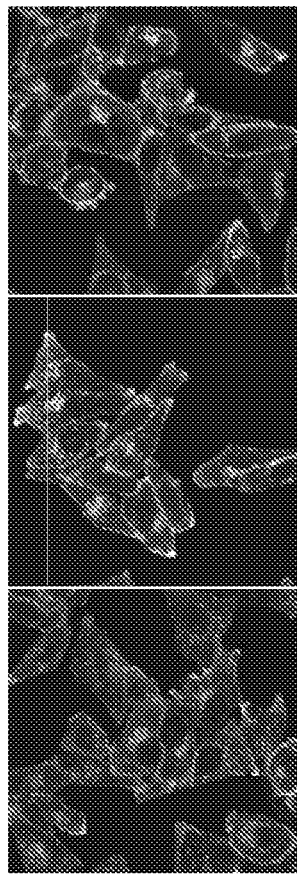
CF647 Mix-n-Stain labeling of mouse anti-transferrin receptor antibody or isotype control with 10-fold excess of BSA or gelatin, fluorescence microscopy
FIG. 3A  No Stabilizer, Standard Protocol
FIG. 3B  10X BSA, Modified Protocol
FIG. 3C  10X Gelatin, Modified Protocol CF647 Mix-n-Stain with Nanosep® concentration to exchange reaction buffer with antibody storage buffer

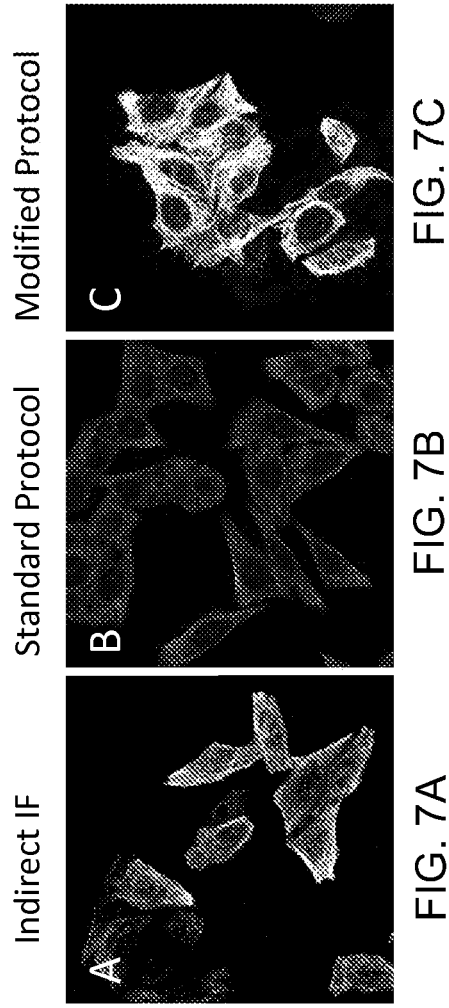
Mix-n-Stain labeling of IgG in ascites fluid analyzed by microscopy
FIG. 7A  Indirect IF
FIG. 7B  Standard Protocol
FIG. 7C  Modified Protocol

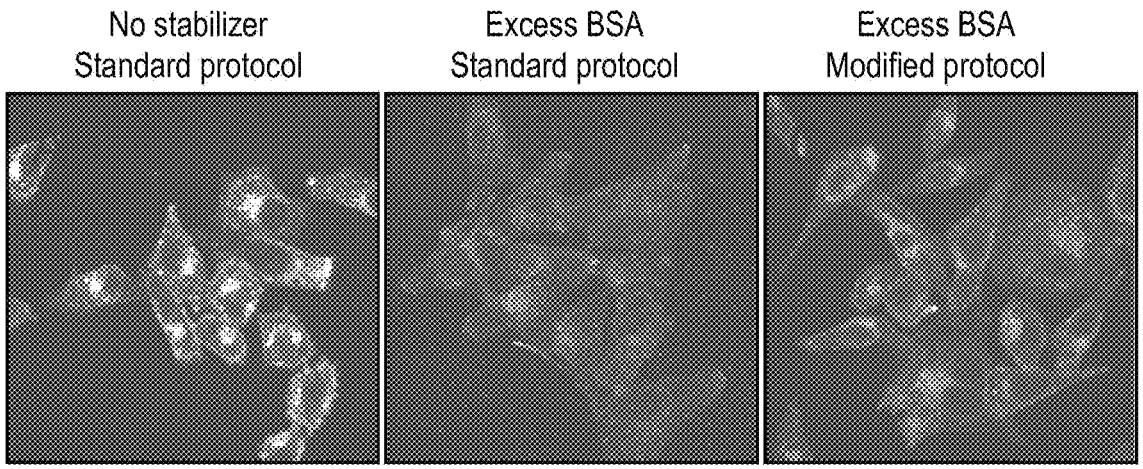
Figure 8A  
No stabilizer  
Standard protocol
Figure 8B  
Excess BSA  
Standard protocol
Figure 8C  
Excess BSA  
Modified protocol
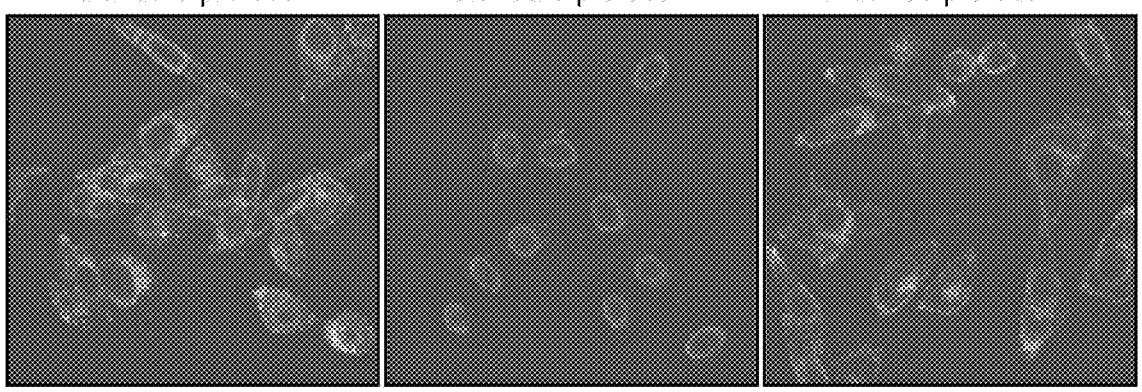
Figure 8D  
No stabilizer  
Standard protocol
Figure 8E  
Excess BSA  
Standard protocol
Figure 8F  
Excess BSA  
Modified protocol
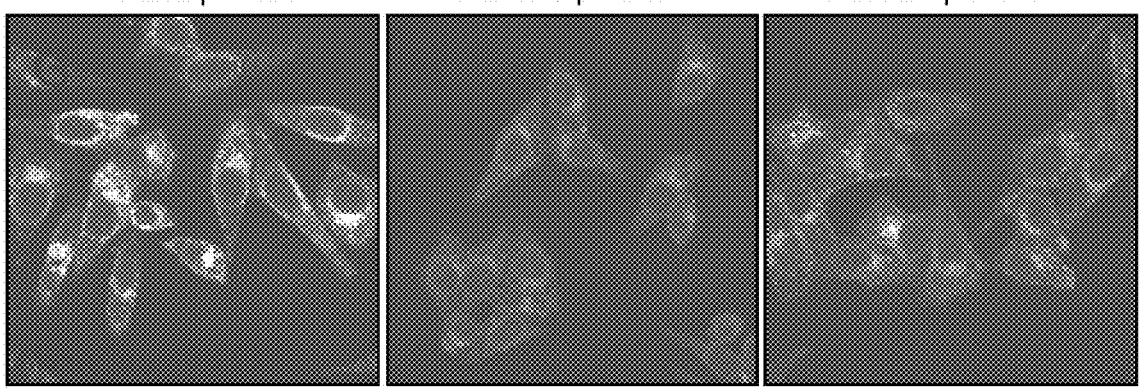
Figure 8G
Figure 8H
Figure 8I

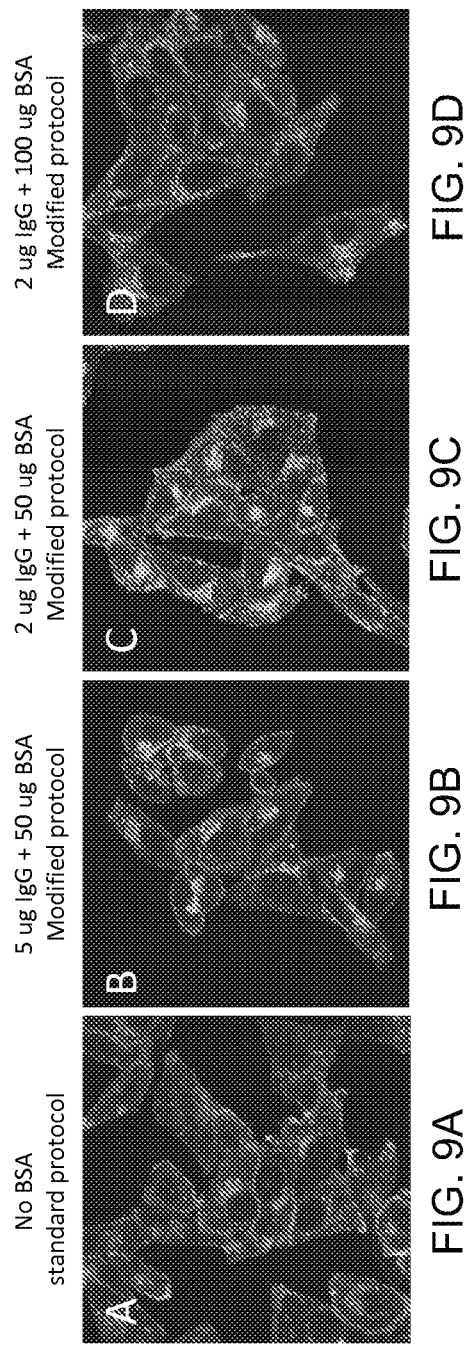

METHODS, COMPOSITIONS AND KITS FOR LABELING OF PROTEINS

CROSS-REFERENCE TO RELATED APPLICATIONS

This application is a continuation of U.S. application Ser. No. 14/030,993, filed Sep. 18, 2013, which claims the priority benefit of U.S. Provisional Application Ser. No. 61/702,729 filed Sep. 18, 2012 which applications are incorporated herein by reference in their entirety.

BACKGROUND OF THE INVENTION

Biological labels such as fluorescent dyes are widely used in biological research and medical diagnostics. Fluorescent dyes are superior to conventional radioactive materials because fluorescent dyes are less expensive and less toxic, and can typically be detected with sufficient sensitivity. Indeed, a diversity of fluorophores with a distinguishable color range has made it more practical to perform multiplexed assays capable of simultaneous detection of multiple biological targets. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay. Moreover, the low toxicity of fluorescent dyes provides ease of handling in vitro, and also renders it safer for imaging biological processes in vivo.

Biological labels for applications described above are often prepared by conjugating a reactive label, such as a reactive dye, to a protein that is capable of binding to a given target or binding partner. The purity of the protein is a critical factor for such a labeling reaction to proceed efficiently. This can be difficult to achieve, particularly with proteins such as antibodies. For example, most commercial antibody products are supplied as a mixture of the antibody and a protein stabilizer such as BSA or gelatin. Moreover, some antibodies are supplied in relatively crude forms, such as ascites fluids and hybridoma cell supernatant, which contain many components besides the antibody. It has been reported that such components can interfere with the labeling reaction and therefore render the results unsatisfactory.

Conventional processes for conjugating dyes to protein binding agents such as antibodies typically require purification of the antibody away from other buffer components, including stabilizers, prior to the conjugation reaction. Purification of the labeled antibody may also have to be performed once the reaction is complete. Purification steps are generally undesirable because preparations of antibody available to a user may contain a very low amount of antibody, and purification may result in loss of valuable antibody. As such, conventional antibody labeling technique is tedious and time consuming.

SUMMARY OF THE INVENTION

There remains a considerable need for methods and compositions that allow for more efficient process of protein labeling. The present invention addresses this need and provides related advantages as well.

Provided herein is a method for labeling a target protein in a mixture in which the target protein is mixed with one or more non-target protein(s), the method comprising: adding an effective amount of reactive label to the mixture under conditions suitable for formation of target-label conjugates in said mixture, wherein the effective amount of reactive label is calculated according to the formula of:

$$W1 + cW1$$

wherein $c = k \times (S_{total}/T)$, wherein k is a value from about 0.1 to about 1.2; $S_{total}$ is the cumulative weight of all non-target protein(s) in a weight unit; T is the total weight of the target protein in the same weight unit as S; W1 is the amount of reactive label required for labeling T amount of the target protein in the absence of any non-target protein to produce a desired degree of target protein labeling; and wherein the conjugates, when used for immunostaining, yield a signal-to-noise ratio that is at least comparable to that of a conjugate labeled by the same reactive label in the absence of the one or more non-target protein(s).

Also provided herein is a method for labeling a target protein in a mixture in which the target protein is mixed with one or more non-target protein(s), wherein the ratio of the cumulative weight of non-target protein(s) to the weight of target protein is at least about 5 but no more than about 50, the method comprising adding an effective amount of a reactive label to the mixture under conditions suitable for formation of target-label conjugates in said mixture, said formation yielding a degree of labeling of the target protein within a range of about 2 to about 20. In one embodiment, the effective amount of reactive label is calculated according to the formula of:

$$W_1 + cW_1$$

wherein c is a constant in the range of about $0.1 \times (S_{total}/T)$ to about $1.2 \times (S_{total}/T)$; $S_{total}$ is the cumulative weight of non-target protein(s); T is the total weight of the target protein; and $W_1$ is the amount of reactive dye used.

For example, the ratio of the cumulative weight of non-target protein(s) to the target protein is at least about 1, about 2, about 3, about 4, about 5 or higher.

Further provided is a method for labeling a target protein in a liquid sample, wherein the target protein in said sample is 5 μg or less, the method comprising adding to the sample: (i) at least about 1 μg of one or more non-target protein(s), and (ii) an effective amount of reactive label to the mixture under conditions suitable for formation of target-label conjugates in said mixture, said formation yielding a degree of labeling of the target protein which is within a range of about 2 to about 20.

In some embodiments, the method comprises adjusting pH of the mixture to neutral pH of about 7. In other embodiments, the target protein is an antibody. In some embodiments, the method comprises adding one or more preservatives. In some embodiments, the method comprises using said target-label conjugates to detect a binding partner of said target. For example, the binding partner is an antigen. In some embodiments, said detecting comprises performing immunostaining.

Further provided herein are mixtures of target-label conjugates prepared by any of the methods described herein. In some embodiments, the target-label conjugates are labeled antibodies, such as primary antibodies.

The invention also provides a method of performing immunostaining comprising: (a) contacting one or more antigen(s) with the mixture of target-label conjugates under conditions suitable for formation of antigen-antibody complexes; and (b) detecting said complexes, thereby performing said immunostaining. In some embodiments, the detecting is performed without reacting said complexes with a secondary antibody. In other embodiments, the one or more antigen(s) are immobilized on a support.

The invention also provides kits for labeling a target protein in a mixture in which the target protein is mixed with one or more non-target protein(s), comprising: (a) a predetermined amount of reactive label, wherein the amount of the reactive label is in excess such that if X μg of the target protein and Y μg of the one or more non-target protein(s) are present in the mixture, then the amount of the reactive label accounts for (X+Y) μg of total protein; and (b) instructions comprising information for user to label the target protein. In some embodiments, the amount of the reactive label permits labeling the target protein with a degree of labeling within a range of about 2 to about 20, about 3 to about 9, or about 3 to about 6.

Further provided herein is a computer-readable medium comprising code that, upon execution by one or more processors, implements a method, the method comprising: (a) selecting an appropriate labeling kit for labeling a target protein mixed with one or more non-target protein(s) in a mixture, wherein said selection is based on the total amount of the target protein and the non-target protein(s) present in the mixture, such that if X μg of the target protein and Y μg of the one or more non-target protein(s) are present in the mixture, then a kit suitable for labeling (X+Y) μg of total protein is chosen for labeling the target protein in said mixture. In some embodiments, the kit permits labeling the target protein with a degree of labeling within a range of about 2 to about 20, about 3 to about 9, or about 3 to about 6.

Also provided is a computer implemented method for selecting a kit for labeling a target protein, comprising: (a) providing a list of kits for labeling target protein of a given amount, wherein the target protein is present in a mixture containing one or more non-target protein(s); (b) receiving request from an inquirer to select a kit for labeling the target protein of the given amount; (c) selecting with the aid of a processor that is programmed to select an appropriate labeling kit for labeling the target protein based on the total amount of the target protein and the one or more non-target protein(s) present in the mixture, such that if X μg of the target protein and Y μg of the one or more non-target protein(s) are present in the mixture, then a kit suitable for labeling (X+Y) μg of total protein is chosen for labeling the target protein. In some embodiments, the kit permits labeling the target protein with a degree of labeling within a range of about 2 to about 20, about 3 to about 9, or about 3 to about 6.

Further provided herein is a method for labeling a target protein in a mixture in which X μg of target protein is mixed with Y μg of one or more non-target protein(s), the method comprising: adding an effective amount of reactive label to the mixture under conditions suitable for formation of target-label conjugates in said mixture, wherein the effective amount of reactive label is provided by the formula:

$$W1[(X+Y)/(X)]$$

wherein W1 is the amount of reactive label required for labeling X μg of target protein; and wherein the conjugates, when used for immunostaining, yield a signal-to-noise ratio that is at least comparable to that of a conjugate labeled by the same reactive label in the absence of the one or more non-target protein(s).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows the geometric mean fluorescence of the cell populations.

FIG. 3A shows HeLa cells stained with Mix-n-Stain labeled anti-transferrin receptor antibody. FIG. 3A shows the standard conjugate, evidencing plasma membrane and punctate intracellular staining typical of transferrin receptor protein localization.

FIG. 3B shows that conjugates labeled in the presence of excess BSA using the modified Mix-n-Stain protocol show similar staining patterns as the standard conjugate of FIG. 3A.

FIG. 3C shows that conjugates labeled in the presence of excess gelatin using the modified Mix-n-Stain protocol show similar staining patterns as the standard conjugated of FIG. 3A.

FIG. 5A shows a flow cytometry analysis representing geometric mean fluorescence of cell populations.

FIG. 7A shows indirect immunostaining with unlabeled mouse anti-tubulin antibody in ascites fluid followed by CF488A goat anti-mouse IgG (gain 467).

FIG. 7B shows direct immunofluorescence staining with CF488A Mix-n-Stain labeled mouse anti-tubulin in ascites fluid labeled using a standard protocol (gain 940).

FIG. 7C shows direct immunofluorescence staining with CF488A Mix-n-Stain labeled mouse anti-tubulin in ascites fluid labeled using a protocol of the invention (gain 767).

FIG. 8A shows a protocol of the invention which improves labeling with rapid antibody labeling kits and reactive dyes from different manufacturers in the presence of excess stabilizer protein. FIG. 8A shows a first dye and no stabilizer under the standard protocol.

FIG. 8B shows a protocol of the invention which improves labeling with rapid antibody labeling kits and reactive dyes from different manufacturers in the presence of excess stabilizer protein. FIG. 8B shows a first dye and BSA stabilizer under the standard protocol.

FIG. 8C shows a protocol of the invention which improves labeling with rapid antibody labeling kits and reactive dyes from different manufacturers in the presence of excess stabilizer protein. FIG. 8C shows a first dye and BSA stabilizer under the modified protocol.

FIG. 8D shows a protocol of the invention which improves labeling with rapid antibody labeling kits and reactive dyes from different manufacturers in the presence of excess stabilizer protein. FIG. 8D shows a second dye and no stabilizer under the standard protocol.

FIG. 8E shows a protocol of the invention which improves labeling with rapid antibody labeling kits and reactive dyes from different manufacturers in the presence of excess stabilizer protein. FIG. 8E shows a second dye and BSA stabilizer under the standard protocol.

FIG. 8F shows a protocol of the invention which improves labeling with rapid antibody labeling kits and reactive dyes from different manufacturers in the presence of excess stabilizer protein. FIG. 8F shows a second dye and BSA stabilizer under the modified protocol.

FIG. 8G shows a protocol of the invention which improves labeling with rapid antibody labeling kits and reactive dyes from different manufacturers in the presence of excess stabilizer protein. FIG. 8G shows a third dye and no stabilizer under the standard protocol.

FIG. 8H shows a protocol of the invention which improves labeling with rapid antibody labeling kits and reactive dyes from different manufacturers in the presence of excess stabilizer protein. FIG. 8H shows a third dye and BSA stabilizer under the standard protocol.

FIG. 8I shows a protocol of the invention which improves labeling with rapid antibody labeling kits and reactive dyes from different manufacturers in the presence of excess stabilizer protein. FIG. 8I shows a third dye and BSA stabilizer under the modified protocol.

FIG. 9A shows a standard conjugate which showed plasma membrane and punctate intracellular staining typical of transferrin receptor protein localization.

FIG. 9B shows conjugates labeled in the presence of 10-fold excess BSA using a protocol of the invention showed similar staining patterns as the standard conjugate.

FIG. 9C shows conjugates labeled in the presence of 25-fold excess BSA using a protocol of the invention showed similar staining patterns as the standard conjugate.

FIG. 9D shows conjugates labeled in the presence of 50-fold excess BSA using a protocol of the invention showed similar staining patterns as the standard conjugate.

DETAILED DESCRIPTION OF THE INVENTION

Figure 1:
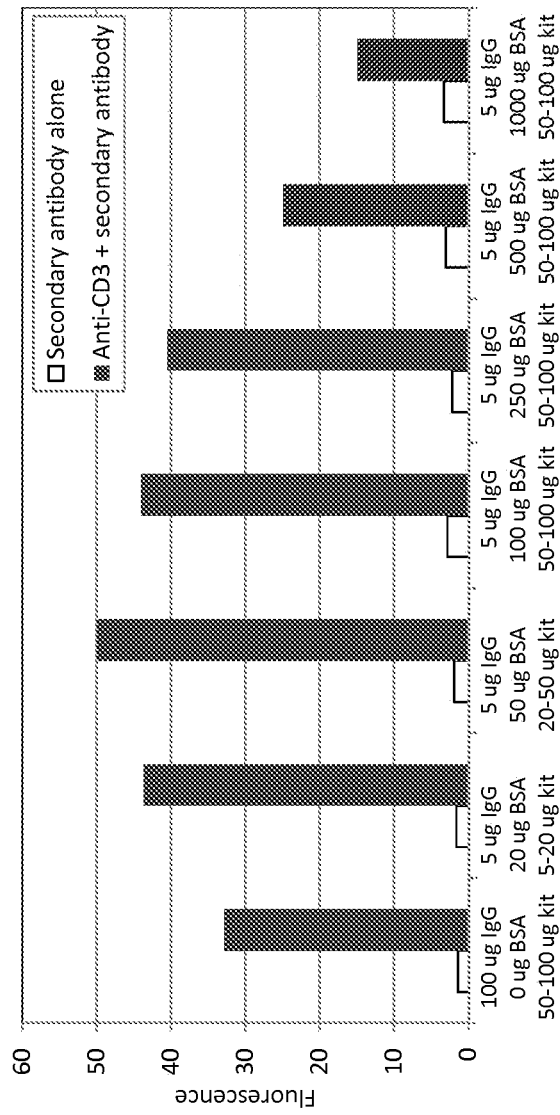
FIG. 1 depicts a comparison of the performance of antibodies labeled with CF633 Mix-n-Stain kits in the presence of excess stabilizer protein. Bars represent the geometric mean fluorescence of the cell populations.

The present invention addresses a need for methods and compositions that allow for more efficient process of labeling protein with a desirable degree of labeling. The subject method is particularly useful in labeling target protein of very low quantity by, e.g., eliminating the necessity of purifying the target protein before and/or after the labeling step.

As used herein, the term "target-label conjugate" or "conjugate" or "labeled protein" represents any molecule where the label is covalently attached to the target molecule. A target that can be labeled by a method of the present invention can be member of a binding pair, such as a ligand, receptor, antigen or an epitope thereof.

In one embodiment, the present invention provides a method for labeling a target protein in a mixture in which the target protein is mixed with one or more non-target protein(s), the method comprising: adding an effective amount of reactive label to the mixture under conditions suitable for formation of target-label conjugates in said mixture, wherein the effective amount of reactive label is calculated according to the formula:

$$W_1 + cW_1$$

wherein c is a constant in the range of about $0.1 \times (S_{total}/T)$ to about $1.2 \times (S_{total}/T)$ $S_{total}$ is the cumulative weight of all non-target protein(s);

T is the total weight of the target protein; and $W_1$ is the amount of reactive label suggested by a manufacturer; wherein the conjugates, when used for immunostaining, yield a signal-to-noise ratio that is at least comparable to that of a conjugate labeled by the same reactive label in the absence of the one or more non-target protein(s).

In another embodiment, the present invention provides a method for labeling a target protein in a mixture in which the target protein is mixed with one or more non-target protein(s), wherein the ratio of the cumulative weight of all non-target protein(s) to the weight of target protein is at least about 5 but no more than about 50, the method comprising: adding an effective amount of a reactive label to the mixture under conditions suitable for formation of target-label conjugates in said mixture, said formation yielding a degree of labeling of the target protein within a range of about 2 to about 20.

In yet another embodiment, the present invention provides a method for labeling a target protein in a liquid sample, wherein the target protein in said sample is 5 μg or less, the method comprising adding to the sample: (i) at least about 1 μg of one or more non-target protein(s), and (ii) an effective amount of reactive label to the mixture under conditions suitable for formation of target-label conjugates in said mixture, said formation yielding a degree of labeling of the target protein which is within a range of about 2 to about 20.

A sample of target proteins to be labeled by any method disclosed herein can contain only one type of target protein or multiple types of target proteins with different binding specificity. For example, a sample of polyclonal antibodies is a mixture of antibodies that bind to different epitopes but share the same or different target specificity. Thus, for the purpose of the invention, when the term "target protein" applies to a polyclonal antibody, it is meant to include an entire collection of antibody molecules that have similar or different target specificity.

Antibodies that can be labeled by a subject method include immunoglobulin molecules and immunologically active portions of immunoglobulin molecules, i.e., molecules that contain an antigen-binding site which specifically binds ("immunoreacts with") an antigen. Non-limiting examples include whole antibodies, antibody fragments, recombinant antibodies, non-human antibodies, chimeric antibodies, humanized antibodies, or fully human antibodies. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

The sample of the invention may comprise at least one non-target protein in addition to said target protein. Herein the term "non-target proteins" means proteins or polypeptides that do not act as a binding agent capable of binding to the same counterpart as the target protein does. According to some embodiments of the invention, the sample may comprise a target protein and at least one non-target protein which can be a stabilizing agent, wherein the weight ratio of total non-target protein(s) over target protein can be any number greater than zero. In other words, the amount of non-target protein(s) can be substantial, sometimes overwhelming, relative to the amount of the target protein, and as such there is still no need to remove the non-target protein(s) from the sample before labeling of the target protein. For example, the ratio of the cumulative weight of non-target protein(s) to the weight of target protein may be $\geq 1/2$, $\geq 1:1$, $\geq 2:1$, $\geq 4:1$, $\geq 5:1$, $\geq 6:1$, $\geq 10:1$, $\geq 20:1$, $\geq 50:1$, $\geq 100:1$ or $\geq 1000/1$.

Many commercial antibody products, including primary antibody products, are often supplied as a mixture of an antibody and one or more non-target proteins for various reasons. In some cases, an antibody is supplied as a mixture of the antibody and a non-target protein which is a stabilizing agent, which can include BSA and/or gelatin. Antibodies at a relatively dilute concentration tend to be unstable due to loss of protein structure conformation, and addition of a stabilizing agent such as BSA or gelatin to a dilute antibody solution helps preserve the integrity of the antibody structure, thus greatly extending the shelf-life of the antibody. Many commercial antibody products comprising a stabilizing agent as a antibody stabilizer have a weight ratio of stabilizing agent (e.g. BSA or gelatin) to antibody which is from about 2:1 to about 10:1. For example, many commercial antibodies are supplied as a 1 mg/mL solution containing 0.5% or 1% BSA or gelatin, which correspond to a BSA or gelatin to antibody weight ratio of 5 to 1 or 10 to 1, respectively.

In some embodiments, the target protein is an antibody in an ascites fluid sample. A large number of commercial monoclonal antibodies are supplied as ascites fluids, which are a relatively crude form of antibody products. Ascites fluids typically comprise a variety of non-target proteins in addition to the antibodies of interest. Ascites is a common and preferred method for producing monoclonal antibodies in a highly concentrated and stable form. Many cell lines that are difficult to scale up into cell culture systems perform very well in ascites production. In this method, hybridoma cells are injected into the peritoneal cavity of an animal (mouse or rat, for example), where the cells multiply and produce fluid (ascites) in its abdomen. This fluid contains a high concentration of antibody which can be harvested. Antibodies in ascites fluids have generally been unsuitable for direct chemical conjugation (without purification) using conventional labeling techniques, because of the interference from the complex mixture of non-target proteins in the fluids. The present invention circumvents this problem to allow direct labeling of antibodies in ascites without first purifying the antibodies from the other substances in the ascites.

In some embodiments, the sample of the invention may be an antibody in a hybridoma cell supernatant. As an alternative to the ascites method, monoclonal antibodies can also be produced by growing hybridoma cells in vitro. Like ascites, hybridoma cell supernatants also typically comprise other non-antibody proteins. The subject labeling technique can directly label antibodies in a hybridoma cell supernatant without first purifying the antibodies from such supernatant.

In some embodiments, the sample comprising the target protein may also comprise a low-molecular-weight amine-containing agent (i.e., MW<1000), such as Tris buffering agent and amino acids, and/or thiols, such as DTT. For example, some commercial antibodies may be supplied in Tris buffer. According to the conventional labeling methods, these amine-containing agents or thiols may interfere with the labeling reaction when present at relatively high concentration. In such a case, such sample may be required for a pretreatment process to remove the low-molecular-weight interfering agents. Such cumbersome pretreatment process may include ultramembrane filtration using a Nanosep vial or the equivalent. In some embodiment, the present invention eliminates the need of such pretreatment process even when the target protein is mixed with low-molecular weight amine containing agent.

The subject labeling method utilizes detectable labels. Detectable labels are generally molecules that can directly or indirectly produce or result in a detectable signal either by themselves or upon interaction with another molecule. The term "reactive detectable label" (RDL) or "reactive label" used interchangeably herein, refers to a detectable label comprising a reactive group that is capable of forming a covalent bond with a target protein.

In some embodiments, detectable labels have a molecular weight of less than about 5000 dalton. Non-limiting examples of detectable label include fluorescent dyes, biotin, degoxigenin, haptens, epitopes, enzymes, fluorescent proteins, metal chelators, chemical moieties comprising radioisotopes, oligonucleotides, chemical moieties suitable for bioorthogonal conjugation. In some embodiments, the detectable labels are dyes or biotin. Dyes useful in labeling proteins are known in the art. In general, a dye is a molecule, compound, or substance that can provide an optically detectable signal, such as a colorimetric, luminescent, bioluminescent, chemiluminescent, phosphorescent, or fluorescent signal. In some embodiments, the dye is a fluorescent dye.

In some embodiments, fluorescent dyes and biotin compounds comprise at least one net negative charge after conjugation to said target protein, or at least one poly(ethylene glycol) (PEG) moiety. Fluorescent dyes and biotin labels of such structure features generally have good water solubility, which is desirable for achieving good signal to noise ratio in detections. In some embodiments, fluorescent dyes comprising one or more PEG groups can be used as these dyes that do not impart too many negative charges to the target protein upon conjugation. As a result, a target protein labeled with such PEGylated dye may give a higher signal to noise ratio in detection. Reactive fluorescent dyes comprising PEG groups have been described, for example, in US patent application No. 2009/0305410 which is incorporated herein by reference. A number of trademarked commercial fluorescent dyes are highly water-soluble and thus are useful dyes for the invention. For example, commercial dyes for use the invention include but are not limited to CF dyes (Biotium, Inc.), Alexa Fluor dyes (Invitrogen), DyLight dyes (Thermo Fisher), Cy dyes (GE Healthscience), IRDyes (Li-Cor Biosciences, Inc.), and HiLyte dyes (Anaspec, Inc.). In some embodiments, the excitation and/or emission wavelengths of the dye are between 350 nm to 900 nm, or between 400 nm to 700 nm, or between 450-650 nm.

In some embodiments, the dye is water soluble. In some embodiments, the dye comprises about, less than about, or more than about 1, 2, 3, 4, 5, 6, 7, 8, 9, 10, or more sulfonate groups. In some embodiments, the dye comprises about, less than about, or more than about 1, 2, 3, 4, 5, 6, 7, 8, 9, 10, or more water-soluble polymer groups, such as polyethylene glycol (PEG). A water soluble polymer group can have any suitable molecular weight, such as 300-10000 Daltons, including 450-5000 Daltons. In some embodiments, a water soluble polymer group has a molecular weight of about, more than about, or less than about 200, 300, 400, 450, 500, 600, 700, 800, 900, 1000, 1500, 2000, 3000, 4000, 5000, 6000, 7000, 8000, 9000, 10000, 20000, 30000, 40000, 50000, or more Daltons, or any range between any two such weights. In some embodiments, the dye is sulfonated and/or pegylated, such as in a sulfonated and/or pegylated coumarin dye, a sulfonated and/or pegylated xanthene dye, a sulfonated and/or pegylated cyanine dye, or a sulfonated and/or pegylated pyrene dye.

Suitable reactive groups include but are not limited to amine-reactive groups, thiol-reactive group and hydroxyl-reactive group. In some embodiments, reactive groups are amine-reactive groups or thiol-reactive groups.

In some embodiments the dye is an amine reactive dye, comprising one or more amine reactive groups that react to form a bond with an amine. In some embodiments, the amine reactive dye comprises about, less than about, or more than about 1, 2, or 3 amine-reactive groups. In some embodiments, the amine reactive group is an activated ester. Examples of activated esters include, but are not limited to, N-hydroxy succinimidyl ester, N-hydroxy sulfosuccinimidyl ester (also frequently referred to as NHS ester or SE), p-sulfo-tetrafluorophenol ester, pentachlorophenol ester, pentafluorophenyl esters, 2,3,5,6-tetrafluorophenol ester, 4-sulfo-2,3,5,6-tetrafluorophenol ester, 2,3,5,6-tetrachlorophenol ester, 4-sulfo-2,3,5,6-tetrachlorophenol ester, other tetrafluorophenyl esters, p-nitrophenyl esters, 2,4-dinitrophenyl ester, 4-nitrophenyl ester, 3-Hydroxy-3,4-dihydro-4-oxo-1,2,3-benzotriazine (HODhbt), carboxylic acids activated using common carbodiimides such as but not limited to diisopropylcarbodiimide (DIPCDI), N,N'-dicyclohexylcarbodiimide (DCC), 1-ethyl-3-(3'-dimethylaminopropyl)carbodiimide hydrochloride (EDC); and carboxylic acids activated with an uronium salt or a phosphonium salt, such as but not limited to O-Benzotriazole-N,N,N',N'-tetramethyluronium hexafluorophosphate (HBTU), O-(Benzotriazol-1-yl)-N,N,N',N'-tetramethyluronium tetrafluoroborate (TBTU), 2-(6-Chloro-1H-benzotriazole-1-yl)-1,1,3,3-tetramethyluronium hexafluorophosphate (HCTU), (2-(6-Chloro-1H-benzotriazole-1-yl)-1,1,3,3-tetramethylaminium tetrafluoroborate) (TCTU), 2-(1H-7-Azabenzotriazol-1-yl)-1,1,3,3-tetramethyl uronium hexafluorophosphate (HATU), 1-benzotriazolyoxytris-(dimethylamino)phosphonium hexafluorophosphate (BOP) benzotriazol-1-yl-oxytripyrrolidinophosphonium hexafluorophosphate (PYBOP); or combinations thereof.

Non-limiting examples of thiol-reactive groups include maleimide, methanethiosulfonate (MTS), 2-pyridyldisulfide and haloacetyl.

Where desired, a linker group between the reactive group and the detectable label can be utilized. In some embodiments, a method of the invention is performed using a bifunctional crosslinker. Bifunctional crosslinkers for use in the invention generally comprise two reactive groups capable of reacting with target and reporter proteins. For example, at least one of the two reactive groups is an amine-reactive group. In some embodiments, a bifunctional crosslinker comprises an amine-reactive group and a hydrolysis-resistant functional group. The amine-reactive group can react with an amine group within a target protein, thereby conjugating the crosslinker to the amine group of the target protein via an amide bond. The amine-reactive group can be an activated ester as described herein. Any of the activated esters described as suitable for use with the amine-reactive dyes or amine-reactive detectable labels are also suitable for use with the amine-reactive group of the cross-linker. As an example, the activated ester may be an N-hydroxy succinimidyl ester.

Hydrolysis-resistant functional groups can react with the reporter protein, thereby attaching the other end of the crosslinker to the reporter protein. In some embodiments, the functional group is hydrolysis-resistant. For example, a hydrolysis-resistant functional group or hydrolysis-resistant reactive group is at least 90% intact in a buffer, such as a buffer of a methods of the invention, for at least 24 hours, or for at least 1 month, or for at least 3 months. Generally, hydrolysis-resistant functional groups are compatible with the amine-reactive group of the crosslinker such that that they do not react with each other. Where the amine-reactive group is an electrophile, the hydrolysis-resistant functional group of the crosslinker is generally not a nucleophile. Non-limiting examples of functional groups that are hydrolysis-resistant and non-nucleophilic include aldehydes, ketones, azido, alkyne, phosphines participating in Staudinger conjugation, dienes, dienophiles, protected hydrazine and protected aminooxy.

Buffers useful for labeling the target protein with an amine-reactive dye, an amine-reactive detectable label, or with a bifunctional crosslinker in the methods of the invention include any that support a labeling reaction as described herein. In some embodiments, the buffer is an alkaline buffer, having a pH greater than about 7, for example having a pH from about 7 to about 14, such as a pH of about, more than about 7, 7.1, 7.2, 7.3, 7.4, 7.5, 7.6, 7.7, 7.8, 7.9, 8.0, 8.5, 9, 9.5, 10, 10.5, 11, 11.5, 12, 12.5, 13, 13.5, or 14. In some embodiments the buffer has a pH of about, more than about, or less than about 4, 4.5, 5, 5.5, 6, or 6.5. Non-limiting examples of useful buffers include sodium carbonate buffers, sodium bicarbonate buffers, borate buffers, tris buffers, MOPS buffers, HEPES buffers, and combinations thereof. In some embodiments, the buffer is of a concentration such that the combined solution has a pH from about 6 to about 11, such as from about 7.9 to about 9.8, or from about 8 to about 9. In some embodiments, the pH of the combined solution about, more than about, or less than about 6, 6.5, 7, 7.5, 7.6, 7.7, 7.8, 7.9, 8.0, 8.1, 8.2, 8.3, 8.4, 8.5, 8.6, 8.7, 8.8, 8.9, 9.0, 10, 10.5, 11, or more. In some embodiments, the buffer has a starting concentration that is about, more than about, or less than about 2-fold, 5-fold, 10-fold, 20-fold, 30-fold, 40-fold, 50-fold, or more than the concentration of the buffer in the combined solution. In one example, a 10× reaction buffer comprises 500 mM sodium bicarbonate and 100 mM Tris.

In some embodiments, the labeling reaction with a dye, detectable label or crosslinker takes place at temperature of about, less than about, or more than about 4° C., 10° C., 15° C., 16° C., 17° C., 18° C., 19° C., 20° C., 21° C., 22° C., 23° C., 24° C., 25° C., 26° C., 27° C., 28° C., 29° C., 30° C., 37° C., 40° C., 50° C., or higher. In some embodiments, the labeling reaction takes place a room temperature, such as between 15° C.-30° C. In some embodiments, the labeling reaction is completed in less than about 5, 4, 3, 2, 1, or fewer hours; or less than about 60, 45, 30, 25, 20, 15, 10, 9, 8, 7, 6, 5, or fewer minutes. In some embodiments a completed labeling reaction containing a target protein labeled with a detectable label such as a dye, is used, such as in a detection process, without further manipulation, such as without the addition of other reagents, such as a quenching agent, and/or without purification, isolation, or concentration of the labeled target protein. Likewise, in some embodiments, a completed labeling reaction containing a target protein labeled with a crosslinker can be used directly in a subsequent protein-protein conjugation reaction without any purification of the crosslinker-labeled target protein as described herein.

In some embodiments, one or more portions of an amount of labeled protein produced by the labeling reaction are used directly in one or more processes, and unused labeled target protein is stored for later use. In some embodiments, a storage buffer is added to a labeled protein to produce a stored protein solution. In general, a storage buffer is effective in increasing the time following a labeling reaction during which a labeled protein remains stable. In general, a labeled protein is considered "stable" when it retains its activity, or a substantial portion thereof, such as for use in a detection process. In some embodiments, a stored protein is considered stable when about or more than about 30%, 40%, 50%, 60%, 70%, 80%, 85%, 90%, 95%, 97.5%, 99%, 99.5%, 99.9%, or more of the pre-storage activity remains. In some embodiments, the stored labeled protein is stable for about or more than about 1, 2, 3, 4, 5, 6, 7, 8, or more weeks; 1, 2, 3, 4, 5, 6, 7, 8, 9, 10, 11, 12, or more months; or 1, 2, 3, or more years. In some embodiments, a storage buffer comprises one or more stabilizers and/or one or more preservatives. Non-limiting examples of stabilizers include bovine serum albumin, gelatin, and glycerol. Non-limiting examples of preservatives include sodium azide, thimerosal, and other antimicrobial agents. In general, a storage buffer can have either a lower pH or higher pH than the buffer used in the labeling reaction, such that addition of the storage buffer lowers or raises the pH of the combined solution containing the labeled protein. In some embodiments, the pH of a solution containing a stored, labeled protein is about, less than about, or more than about 5.5, 6, 6.5, 7, 7.1, 7.2, 7.3, 7.4, 7.5, 7.6, 7.7, 7.8, 7.9, 8, 8.5, 9, or higher. In some embodiments, the pH of the stored protein solution is between about 6.0-9.0, such as 6.5-8.0, or 7.2-7.5.

In one aspect, the present invention provides methods to determine the appropriate amount of the RDL required for desired labeling of a target protein in the presence of non-target protein(s). Traditionally, only purified target proteins are suitable for covalent labeling. For example, widely practiced antibody labeling protocols from various fluorescent dye reagent companies require the use of purified antibodies. In the case where an antibody is supplied with BSA or gelatin as stabilizer, the BSA or gelatin must be removed using one of several known methods before the antibody can be labeled. For example, the Melon Gel IgG Spin Purification Kit from Thermo Fisher is specifically designed for the purpose of antibody clean-up. Other kits, such as Lightning-Link® antibody labeling kits from Innova Biosciences permit up to 5:1 BSA:antibody weight ratio in the labeling reaction or a BSA concentration of up to 0.5% in the unlabeled antibody solution (See Lightning-Link product information sheet). Although the tolerance of BSA or gelatin present in these kits provides some convenience, antibodies labeled in this manner generally give inferior results (e.g., high noise to signal ratio) to those prepared using purified antibodies. Moreover, existing commercial antibody labeling kits cannot tolerate excess amount of non-target protein, such as non-target protein(s) present at >0.5%. Unfortunately, many commercial antibody products are supplied with as much as 1% BSA or gelatin, which could amount to a non-target protein:target protein ratio of ≥10:1. If samples are ascites fluids, cell supernatants or serum, the ratio of non-target to target protein can be even higher.

In some embodiments, the amount of BSA or gelatin is about, more than about, or less than about 50-fold, 40-fold, 30-fold, 20-fold, 10-fold, 9-fold, 8-fold, 7-fold, 6-fold, 5-fold, 4-fold, 3-fold, 2-fold, 1-fold, or less than the amount of the target protein by weight.

In some embodiments, a method of the invention comprises: 1) providing a sample comprising a target protein and at least one non-target protein; 2) providing a reactive detectable label (RDL) in an amount that is the sum of a desired amount (W1) of RDL required for labeling the target protein in its pure form plus an additional amount (W2) of RDL for each weight equivalent of the total non-target protein(s) to that of the target protein in the sample, wherein W2 is ≥ about 10% W1 but ≤ about 120% W1; 3) combining said sample and said RDL in a buffer suitable for covalent conjugation to form a reaction solution; 4) incubating said reaction solution for a time sufficient for conjugation to form a solution of a labeled target protein; and 5) optionally neutralizing the pH of and adding one or more preservatives and one or more stabilizers to the solution of the labeled target protein.

In some embodiment, the total amount of proteins in the sample (i.e., target protein plus non-target protein) is taken into consideration when calculating the amount of RDL required for the labeling. As a result, the amount of RDL used in the labeling reaction is in proportion to the total amount of proteins in the sample. In general, the amount of RDL used in the labeling reaction is the sum of a desired amount (W1) of RDL required for labeling the target protein in the sample in its pure form plus an additional amount (W2) of RDL for each weight equivalent of the total non-target protein(s) to that of the target protein in the sample. In one embodiment, W2 is at least about 10% W1 but less than about 150% W1. For example, for a sample comprising 10 μg of a target protein and 50 μg of a non-target protein, the amount of RDL would be from W1+10%(50 μg/10 μg)W1 to W1+120%(50 μg/10 μg)W1, or from 1.5 W1 to 7 W1. In some embodiments, W2 is at least about 50% W1 but less than about 120% W1. In some embodiments, W2 is about 100% W1. In some embodiments, the non-target protein(s) and target protein in the sample are all treated as target protein for the purpose of determining the desired amount of RDL required for label the target protein. In some embodiments, one may recognize that there may be a difference between the target protein and non-target protein(s) in the number of functional groups available to react with the RDL. Treating non-target protein(s) as target protein in estimating the amount of RDL required may sometimes produce sub-optimal target protein labeling, in which case, one can titrate the amount of RDL to determine for the optimal condition. Methods of titration are well established in the art and these are not detailed herein.

The amount of a RDL used in the labeling reaction affects the number of the RDL molecule attached to a target protein, which is generally referred to as the degree of labeling ("DOL") of the target protein. In turn, the DOL of the target protein affects the biological activity of the labeled target protein. Too high a DOL may weaken the binding affinity of the target protein and thus lower the detection signal while too low a DOL may also lead to low detection signal because the per-unit signal from each binding pair formation between the labeled target protein and its target will be weak. For a given target protein and detectable label, there is generally a range of DOL, within which the labeled target protein produces the desired result in biological staining. Such a DOL range may be referred to as desired DOL range. Accordingly, the W1 value described above corresponds to an amount of RDL that produces a DOL within the desired range for the given target protein in pure form and RDL. The desired DOL range differs, depending on the nature of the target protein and detectable label. If the target protein is an antibody and the detectable label is a fluorescent dye or other small molecular label, such as a biotin label, the desired DOL range is typically from 1 to about 20, 2 to about 10, or more commonly from 3 to about 9. Specific dye labels may have more specifically or more narrowly defined desired DOL range. For example, for antibody labeling, the recommended DOL for the dye CF488A is from 4 to 9 while the recommended DOL for CF750 is from 3 to 6. Generally, the recommended DOL ranges for labeling antibodies and other common target proteins with most fluorescent dyes and other small molecular labels are known. For example, the individual recommended DOL ranges for using CF dyes, Alexa Fluor dyes, Cy dyes and Dylight dyes to label antibodies are generally listed in the product information sheet accompanying the dye products. Specifically, the following value are known for Alexa Fluor dyes: DOL 1-3 for Alexa Fluor 405, DOL 1-4 for Alexa Fluor 610, DOL 2-4 for Alexa Fluor 633, Alexa Fluor 700, Alexa Fluor 750, DOL 3-5 for Alexa Fluor 568, DOL 3-6 for Alexa Fluor 546, Alexa Fluor 555, Alexa Fluor 594, Alexa Fluor 647, Alexa Fluor 660, Alexa Fluor 680, DOL 3-7 for Alexa Fluor 430, DOL 4-7 for Alexa Fluor 514, DOL 4-8 for Alexa Fluor 350, Alexa Fluor 488, and DOL 5-8 for Alexa Fluor 532.

Moreover, product information sheets generally also provide a recommended W1 value for producing a desired DOL. For example, Thermo Scientific publishes product information sheets for a wide variety of dyes, and the recommended amount of dye (W1 values) to be used. The below exemplifies the suggested amount of dyes by the manufacturer in labeling target proteins of certain concentration (mg/mL). This information provides the basis of W1 of the present invention.

TABLE 2

Amounts of amine-reactive dye to use.

| Dylight Dye | Protein (mg/mL) | Molar-fold Excess | Protein (mg/mL) | Molar-fold Excess |
|---|---|---|---|---|
| 350 | <2-5 | 12.5-15 | ≥5 | 10 |
| 405 | <2-5 | 10-12.5 | ≥5 | 7.5 |
| 488 | <2-5 | 10-15 | ≥5 | 8 |
| 550 | <5 | 10-15 | ≥5 | 8 |
| 594 | <5 | 5-10 | ≥5 | 8 |
| 633 | <5 | 10-12.5 | ≥5 | 7.5 |
| 650 | <5 | 7 | ≥5 | 4 |
| 680 | <5 | 5-8 | ≥5 | 6-7 |
| 755 | <5 | 5-10 | ≥5 | 6-7 |
| 800 | <5 | 5-8 | ≥5 | 6-7 |

Calculate amount (mg) of DyLight NHS Ester Dye to be added to the labeling reaction:

$$\frac{\text{amount of protein (mg)}}{\text{MW of protein}} \times 10 \times \text{MW of fluor} = \underline{\qquad} \text{ mg of fluor}$$

Similarly, Biotium publishes product information sheets for dyes such as CF™ 633 and CF™ 488, for which it recommends a ratio of dye/protein of between 9:1 and 15:1.

For detectable labels that are relatively large in size, such as enzymes and fluorescent proteins, the desired DOL is generally smaller so that the large size of the label does not affect the binding affinity of the labeled target protein. In some cases, the relatively small DOL is a consequence of the conjugation chemistry, where the target protein has only a limited surface area to accommodate more than two large labels. Like fluorescent dye labels, the W1 values for most protein-based labels and common target proteins are well documented in the literature.

The desired DOL ranges and W1 values for new RDLs or new target proteins can be obtained by first preparing labeled target proteins with various DOLs and then testing the conjugates in biological staining. For example, the desired DOL ranges of labeled antibodies can be readily determined using flow cytometry as shown in US patent applications 20090305410 and 20110136201. In principle, any staining assay that involves binding pair formation between a labeled target protein and a binding target can be used for determining desired DOL and W1.

DOL can be determined according to any method known in the art. For example, a typical procedure for determining DOL begins with a measurement of the $A_{280}$ and $A_{max}$ of the dye-labeled protein. Excess dye is first removed from the sample by dialysis or gel filtration. The nonconjugated dye is removed to improve the accuracy of the determination. The absorbance of the dye-labeled protein is measured at 280 nm using a spectrophotometer ("$A_{280}$"). Then, the absorbance of the dye-labeled protein ("$A_{max}$") is measured at the $\lambda_{max}$ of the dye. Next, the DOL is calculated as follows:

Protein concentration=$[[A280-(A_{max} \times CF)] \times$dilution factor$]/\varepsilon$, where $\varepsilon$ is a protein molar extinction coefficient, CF is a correction factor which accounts for the amount of absorbance at 280 nm caused by the dye, and the dilution factor is the extent to which the labeled protein sample was diluted for absorbance measurement.

Finally, the DOL is determined as $[A_{max} \times$dilution factor$]/[\varepsilon' \times$dilution factor$]$, where $\varepsilon'$ is the molar extinction coefficient of the fluorescent dye.

The target protein and RDL are combined in a buffer to react. The buffer generally serves to maintain a pH range favorable for the labeling reaction. A desired pH range for amine/activated ester reaction is generally from about 7 to about 10, more generally from about 7.4 to about 9.5. In some preferred embodiments, the buffer for amine/activated ester reaction has a pH from about 8 to about 9. Preferably, the pH 8-9 buffer is selected from the group consisting of bicarbonate buffer, Tris buffer, borate buffer and any combination thereof. A desired pH range for thiol/thiol-reactive group reaction is generally from about 6 to about 8. In some cases, the buffer for thiol/thiol-reactive group reaction is a pH about 7 PBS or Tris buffer. The desired buffers for labeling reactions involving other reactive groups and functional groups are also known in the art.

The labeling reaction can take place at any temperature in the range from about 4° C. to about 40° C. The lower the temperature at which the reaction is carried out, the longer the reaction time will be. In general, if the labeling reaction is carried out at 4° C., the reaction time may be at least several hours, such as at least 3 hours to 24 hours. In some cases, the labeling reaction can be carried out at 4° C. overnight. The ~4° C. temperature is a common refrigerating temperature used to store biological samples and is sometimes approximated by placing the samples over ice. Where desired, the labeling reaction of the invention is carried out at room temperature for convenience and also for good reaction rate. Depending on the nature of the labeling reaction, the reaction time may be from about 1 minute to about 24 hours. If the RDL is an activated ester, such as a succinimidyl ester, the reaction time may be from about 1 minute to about 2 hours, more typically from about 5 minutes to about 1 hour. In some preferred embodiments, the labeling reaction using an activated ester RDL takes about 15 minutes to about 30 minutes to complete.

During the labeling reaction, the container containing the reaction mixture may be let stand still or agitated via rocking, shaking or stirring.

Upon completion of the labeling reaction, a quencher chemical capable of reacting with the RDL is optionally added to the solution of the labeled target protein to consume any remaining RDL at the end of the labeling reaction. In general, the reaction buffer itself is capable of consuming any remaining RDL. Thus, in some cases, addition of a quencher chemical may not be necessary.

Where desired, pH of the resulting solution of the labeled target protein may be adjusted for long-term storage. In general, unless the labeled target protein is to be immediately used in an biological staining experiment, the labeled target protein solution can be adjusted to a relatively neutral pH, such as pH 6.8-7.8, by adding either a base or acid. Optionally, a preservative, such as sodium azide, and a protein stabilizer, such as BSA or gelatin, are also added so that the labeled target protein can be stored without significant activity loss during long-term storage, such as at least a 3-month storage, at least a 6-month storage or at least a 1-year storage.

A major advantage of the labeling method of the invention is the ability to optimally label a target protein with a desired RDL in the presence of virtually any amount of one or more non-target proteins. In the present invention, competition for RDL from non-target protein(s) has been taken into account by providing an extra amount of RDL so that the target protein is labeled with desired DOL.

In another embodiment, the invention provides a method of labeling a target protein on a micro scale. Herein the amount of the target protein to be labeled is usually <5 μg, more commonly ≤1 μg, sometimes ≤0.1 μg, or even ≤0.01 μg. The method of labeling comprise the following steps: 1) providing a target protein sample comprising <5 μg of said target protein; 2) Providing a separate non-target protein in an amount that is at least $\frac{1}{10}^{th}$ the amount of the target protein; 3) adding to said sample a RDL in an amount that is sufficient to produce a labeled target protein with desired DOL; 4) combining said sample, said separate non-target protein and said RDL in a buffer suitable for covalent conjugation to form a reaction solution; 5) incubating said reaction solution for a time sufficient for conjugation to form a solution of labeled target protein; and 6) optionally neutralizing the pH of and adding one or more preservative and one or more stabilizer to the solution of the labeled target protein.

In some embodiments, the amount of the separately provided non-target protein is ≥1 μg but ≤20 μg. In another embodiment, the amount of the target protein in the sample is ≤1 μg and the total amount of the protein(s) in the sample together with the separately provided non-target protein is in the range from 1 μg to about 10 μg, more preferably from about 5 μg to about 10 μg.

In some embodiments, the amount of RDL provided is in excess of what is generally required for labeling the amount of the target protein in pure form but less than an amount of RDL that over-labels the target protein. As describes above, the desired amount of RDL can be readily determined by testing labeled target protein conjugates prepared by using incremental amounts of RDL in the labeling. However, a more practical and preferred way is to treat the total amount of proteins (i.e., target protein plus non-target protein) as the amount of target protein and then determine the amount of RDL required.

This method of the present invention overcomes multiple problems one may encounter when covalently labeling a very small and sometimes very valuable amount of a target protein. For example, when the amount of the target protein is <5 µg, there are generally no pre-formulated commercial labeling kits available. The end-user is therefore required to measure and mix very small quantities of multiple components in order to carry out micro-scale labeling each time. If the amount of target protein is even lower, such as ≤1 µg, the challenge of measuring and mixing minute quantities of reaction components in an accurate manner can be too great to overcome. Although one may dilute the components to facilitate the measuring and mixing, the rate of the labeling reaction with dilute components can be orders of magnitude slower because the product of reactant concentrations (i.e., [target protein][RDL]), which governs the reaction rate, can become much smaller. Moreover, in a dilute solution, RDL degradation due to hydrolysis becomes important, which further lowers the labeling efficiency. In the present invention, a non-target protein is added as a "filler" so that a micro scale target protein labeling can be conducted on a more normal scale for improved reliability.

In another embodiment, the invention provides a method of staining a biological sample comprising or thought to comprise a binding partner, the method comprising the steps of:

1) Adding an aliquot of a solution of a labeled target protein prepared according to one of the two methods above to a biological sample in a media, wherein the biological sample comprises or is thought to comprise a binding partner; 2) Incubating the sample for a time sufficient for the labeled target protein and the binding partner to form a binding complex; and 3) Washing the sample with a buffer to remove unbound labeled target protein, labeled non-target protein and any unconjugated detectable label, resulting in a stained biological sample.

The biological sample herein may be in one of many possible formats. Nonlimiting examples include cell cultures, tissue cultures, electrophoresis gels, blotting membranes and a solid surface immobilized with a binding partner.

The resulting stained biological sample may be subject to downstream analyses, including viewing, detecting, and/or further staining with one or more agents. For example, if the detectable label is fluorescent dye, the stained sample may be directly analyzed by fluorescent microscopy, flow cytometry, microplate reader assay, western blotting. If the detectable label is a biotin label, detection can be carried out after the sample is further stained by a fluorescently labeled streptavidin.

Kits

In one aspect, the invention provides kits containing any one or more of the elements disclosed in the above methods and compositions.

In one embodiment, provided is a kit for labeling a target protein in a mixture in which the target protein is mixed with one or more non-target protein(s), comprising a predetermined amount of reactive label, wherein the amount of the reactive label is in excess such that if X µg of the target protein and Y µg of the one or more non-target protein(s) are present in the mixture, then the amount of the reactive label accounts for (X+Y) µg of total protein; and instructions comprising information for user to label the target protein.

For example, the amount of the reactive label permits labeling the target protein with a degree of labeling within a range of about 2 to about 20, about 3 to about 9, or about 3 to about 6.

Conventional antibody labeling kits typically contain a reactive label, a reaction buffer, a purification device or material and manual. Some of the kits are formulated for labeling a specific weight range of an antibody. For example, Innova Biosciences, Inc. offers various sizes of so-called Lightening-Link® antibody labeling kits for labeling antibodies with quantities in the range of 10-20 µg, 100-200 µg and 1-2 mg, respectively. These kits are primarily designed for labeling purified antibodies without the presence of non-antibody proteins. Although some of the kits can tolerate the presence of certain level of BSA or gelatin in the labeling reaction, the tolerance is generally at the expense of the antibody labeling quality. In accordance to the present invention, much improved labeling results can be obtained if the labeling protocol is modified to treat the total amount of the proteins in the sample (i.e., the weight of antibody plus the weight of non-antibody protein(s)) as the weight of the antibody in determining the amount of the RDL to use or the size of the labeling kit to select, as described herein. For example, a 20 µL antibody sample containing 1 mg/mL antibody and 0.5% BSA, which amounts to about 20 µg antibody and 100 µg of BSA or 120 µg total proteins, would be best matched with a 100-200 µg sized Lightning-Link antibody labeling kit, instead of a 10-20 µg sized kit, which the manufacturer would have recommended. As another example, a 10 µL antibody sample containing 1 mg/mL antibody and 1% BSA, which corresponds to 10 µg antibody and 100 µg BSA or 110 µg total proteins, would be well labeled with a 100-200 µg sized Lightning-Link kit. However, based on the product descriptions for Lightning-Link from the manufacturer, the antibody sample would not have been even be suitable for direct labeling because the non-target protein to target protein weight ratio is 10:1, which far exceeds the 5:1 limit set by the kits. In yet another example, a 1 µL antibody sample containing 1 mg/mL antibody and 1% gelatin, which corresponds to about 1 µg antibody and 10 µg gelatin or 11 µg total proteins, would be well labeled with either a 10-20 µg sized Lightning-Link kit. If one were to follow manufacturers' recommended protocols, the 10-20 µg sized Lightning-Link kit would have been suitable for the small antibody sample because the 1 µg antibody quantity is far below the kit size. Additional examples and results are shown in FIGS. 1, 2A-B, 3A-C, 4A-B, 5A-D, 6, and 7A-C and in the Example section.

In addition, provided herein are kits comprising one or more RDL, one or more reaction buffer suitable for labeling reaction, one or more vials of a storage buffer, and an instruction manual with a labeling protocol according to the invention, and optionally comprising a vial of a "filler" non-target protein and an ultramembrane filtration device for removing amine-containing small molecules and/or concentrating solutions. In some embodiments, the amount of RDL is pre-measured for labeling a specified amount of protein(s). Preferably, the specified amount of protein(s) that can be labeled is expressed in form of a weight range, such as 5-20 µg, 20-50 µg, 50-100 µg, 10-20 µg, 100-200 µg and 1-2 mg.

In some embodiments, the kit comprises one or more elements for carrying out a method of the invention, the elements in one or more containers. In one embodiment, a kit for labeling a target protein with a dye or detectable label comprises a buffer; one or more reactive dye or detectable label for labeling one or more target proteins; optionally a storage buffer; and instruction in one or more languages, for example in more than one language. The reactive dye or detectable label may be a reactive dye, a reactive biotin, a reactive digoxigenin or a reactive epitope. The dye can be any of the dyes described herein, including but not limited to an amine reactive dye. The buffer can be any of the buffers described herein, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. The amine can be any amine described herein, including but not limited to Tris. In some embodiments, the dye comprises one or more activated esters, one or more sulfonates, and/or one or more water-soluble polymers, as described herein. In some embodiments, the buffer and dye are sufficient in amount to permit labeling of 5 µg to 200 µg of a target protein, such that the DOL of the labeled target protein is from 1 to about 20. The storage buffer can be any of the storage buffers described herein, and may comprise a stabilizer and/or a preservative as described herein.

In some embodiments, the kit does not comprise a separation device for purifying a target protein before labeling.

In some embodiments, the kit further comprises a stain stabilizing reagent for enhancing dye fluorescence, such as by enhancing fluorescent intensity or reducing a rate of decrease in fluorescent intensity. Stain stabilizing reagents are known in the art, non-limiting examples of which include EverBrite (Biotium), Vectashield (Vector Laboratories), and SlowFade Gold (Invitrogen). In some embodiments, fluorescent intensity of a dye in the presence of the stain stabilizing reagent is increased by at least about 10%, 20%, 30%, 40%, 50%, 60%, 70%, 80%, 90%, 100%, 150%, 200%, 300%, 400%, 500% or more above the intensity of the dye in the absence of the stain stabilizing reagent. In some embodiments, fluorescent intensity of a dye in the presence of the stain stabilizing reagent is maintained above a threshold level for a time that is at least about 0.5, 1, 2, 3, 4, 5, 6, 7, 8, 9, 10, 15, 20, 25, 30, 35, 40, 45, 50, 55, 60, or more minutes. In some embodiments, the threshold level is at least about 10%, 20%, 30%, 40%, 50%, 60%, 70%, 75%, 80%, 85%, 90%, 95%, 96%, 97%, 98%, 99%, 99.5%, or more of the starting fluorescent intensity.

In various embodiments, a fixed amount of reactive label is used to label a target protein in any amount within a certain range, resulting in a labeled target protein that avoids being either under labeled or over labeled. For example, the sample solution comprises between about 1 µg and about 1000 µg, or between about 5 µg and about 200 µg, or between about 5 µg and about 20 µg, or between about 20 µg and about 50 µg, or between about 50 µg and about 100 µg, or between about 50 µg and about 200 µg, or between about 100 g and about 200 µg of said target protein. In some embodiments, the amount of target protein in a sample solution is between about 0.1 µg-10000 µg. In some embodiments, the amount of target protein in a sample is about, less than about, or more than about 0.001, 0.01, 0.1, 1, 2, 3, 4, 5, 6, 7, 8, 9, 10, 15, 20, 25, 50, 100, 150, 200, 250, 500, 1000, 1500, 2000, 3000, 4000, 5000, 6000, 7000, 8000, 9000, 10000, or more micrograms (µg).

The ratio of amount of protein in microgram (µg) to the amount of reactive dye in nanomole (nmol) may be, for example, from 30:1 to 1:1. The sample solution may further comprise one or more non-target proteins. For example, the ratio of the combined weight of target and non-target protein in microgram (µg) to the amount of reactive dye in nanomole (nmol) may be from 30:1 to 1:1. In various embodiments, the ratio of the weight in microgram (µg) of target protein to non-target protein is from about 10:1 to about 1:10.

Uses of the Labeled Proteins of the Invention

Labeled proteins of the present invention can be used as indicators of the presence, absence, relative abundance, and/or amount of a biological target, such as may be found in a biological sample or organism, for example by use in a detection process. In one aspect, the invention provides a method for staining one or more biological targets. In one embodiment, the method comprises (a) preparing one or more labeled proteins according to a method of the present invention, wherein each of said one or more labeled proteins comprises a targeting moiety that binds to a binding partner associated with one or more of said biological targets; and, (b) exposing said one or more biological targets to said one or more labeled proteins, such that said labeled protein binds to said binding partner thereby staining said one or more biological targets. In some embodiments, step (b) is performed without purification of the one or more labeled proteins. In some embodiments, step (a) is not terminated by the addition of a quencher.

In general, a biological sample refers to any biological tissue or fluid. In some embodiments, samples include, but are not limited to, cells in culture, bone marrow; blood; blood cells (e.g., white blood cells, red blood cells, etc.); ascites; tissue or fine needle biopsy samples; cell-containing body fluids; free floating nucleic acids; sputum; urine; cerebrospinal fluid, peritoneal fluid; pleural fluid; washings or lavages such as a ductal lavages or broncheoalveolar lavages; aspirates; scrapings; bone marrow specimens; tissue biopsy specimens; surgical specimens; other body fluids, secretions, and/or excretions; and/or cells therefrom. In some embodiments, a sample comprises cells obtained from a patient. The cells may be, for example, from blood, bone marrow, and/or from tissue derived from solid organs, such as brain, spleen, bone, heart, vascular, lung, kidney, liver, pituitary, endocrine glands, lymph node, dispersed primary cells, tumor cells. Biological samples may include sections of tissues, including but not limited to frozen or fixed sections taken for histological purposes. In some embodiments, a sample may be a body fluid, including, but not limited to, blood fluids, lymph, ascitic fluids, gynecological fluids, and urine. Samples may be obtained from a subject by any of a wide variety of methods known in the art, including without limitation biopsy (e.g., fine needle aspiration or tissue biopsy), surgery, and collection of body fluid (e.g., blood, lymph, etc.). Biological samples also include any material derived by processing any of the above samples. Derived samples may, for example, include nucleic acids or proteins extracted from the biological sample, or obtained by subjecting the sample to techniques such as amplification or reverse transcription of mRNA, or isolation and/or purification of certain components.

In some embodiments, staining of the one or more biological target is performed in vivo or in vitro. Many methods for staining or otherwise detecting a biological target using binding partners are known in the art, and include without limitation immunostaining, immunohistochemistry, immunosorbent assays (e.g. ELISA, with or without a linked enzyme), flow cytometry, fluorescence activated cell sorting (FACS), microarray (e.g. protein array), and other binding partner assays whereby the presence of a binding partner is indicated by retention by an organism, sample, or portion thereof of the one or more labeled protein (e.g. Western blot). In some embodiments, the label carried by the labeled protein is directly observable, such as in a fluorescent dye detectable by exposure to light of a particular frequency or range of frequencies. Typically, excess labeled protein is washed away prior to detection, such that labeled protein that remains is indicative of the presence, absence, relative abundance, and/or quantity of the biological target. Examples of biological targets include, but are not limited to, amino acids, polypeptides, nucleotides, polynucleotides (e.g. DNA or RNA), carbohydrates, lipids, metabolites, cell signaling molecules, cluster of differentiation proteins, hormones, cell surface proteins, intracellular proteins, fragments thereof, and combinations or complexes thereof. In some embodiments, two or more different labeled proteins, each recognizing a different binding partner or set of binding partners are used to detect two or more different biological targets in a single sample or organism. The different labeled proteins typically comprise different targeting moieties, and may or may not comprise the same dye. In some embodiments, each of two or more different labeled proteins are labeled with different dyes, such that exposing two or more biological targets to the two or more differently labeled proteins renders the two or more biological targets optically distinguishable.

In some embodiments, a labeled protein of the invention is used to detect a biological target which is an antigen. The antigen may be, for example, in solution, or the antigen can be bound to a solid substrate. The substrate may be any insoluble support to which the antigen molecule can be bound, either directly or indirectly, which is readily separable from soluble material. The surface of such substrates may be solid or porous, and the substrates may have any shape that allows the substrate to function as expected. Examples of substrates that may be utilized include, but are not limited to, microtiter plates, such as but not limited to ELISA plates; membranes, such as but not limited to, nitrocellulose membranes, PVDF membranes, nylon membranes, acetate derivatives, and combinations thereof; fiber matrix, Sepharose matrix, sugar matrix; plastic chips; glass chips; or any type of bead, such as but not limited to, Luminex beads, Dynabeads, magnetic beads, flow-cytometry beads, and combinations thereof. The substrates are typically formed of glass, plastic or any other type of polymer, such as but not limited to PVC, polyvinyl propylene, polyethylene and the like, polysaccharides, nylon, nitrocellulose, and combinations thereof. Microtiter plates are especially convenient because a large number of assays can be carried out simultaneously, using small amounts of reagents and samples. Where separations are made by magnetism, the support generally includes paramagnetic components, preferably surrounded by plastic.

In some embodiments, stained biological targets are analyzed by western blot. Methods and systems for carrying out Western blots are known in the art. Briefly, this method involves separation of a substrate from other protein by means of a separation medium, such as an acrylamide gel, followed by transfer of the substrate to a membrane (e.g., nylon or PVDF). Presence of the substrate is then detected by labeled binding partners specific for the substrate, such as antibodies, which may in turn be detected by a further binding reagent. Where this first binding partner is a labeled protein, use of further binding reagents may not be necessary. This method enables both quantitation of an amount of substrate and determination of its identity by a relative position on the membrane which is indicative of a migration distance in the separation medium (e.g. during electrophoresis).

In some embodiments, stained biological targets are analyzed by immunohistochemistry. Methods and systems for immunohistochemical analysis are known in the art. In general, detections involving cells include sample fixation and permeabilization, sample blocking with a blocking solution, incubation of the sample with one or more labeled primary binding agents, washing of the stained sample, and detection. Typically, sections of a tissue sample are adhered to a microscope slide. The sample is then exposed to one or more binding agents, each with specificity for one or more targets. Where the one or more binding agents comprise a detectable label, such as a dye, staining is evaluated by detecting the detectable label. Where the one or more binding agents do not comprises a detectable label, the sample are exposed to one or more second binding agents, each with specificity to one or more of the first binding agents and comprising a detectable label, such as a dye. In some embodiments, stained samples are analyzed under a microscope. The combination of exposure to unlabeled binding agent followed by exposure to a second, labeled binding agent can be used in combination with any detection process, for example to amplify a signal.

In some embodiments, the method further comprises visualizing fluorescence of the stained one or more biological targets. Visualization may be by eye, or may be performed by a device, such as a camera, whereby an image is produced. Typically, visualization is performed after a washing step to remove excess labeled protein. In some embodiments, visualization is performed immediately after washing. In some embodiments, visualization is performed at about, before about, or after about 1, 5, 10, 15, 20, 30, 45, 60, 90, 180, or more minutes after washing; 1, 2, 3, 4, 5, 6, 7, 8, 9, 10, 15, 20, 24, or more hours after washing; or 1, 2, 3, 4, 5, 6, 7, 8, 9, 10, 15, 20, 25, 30, 60, or more days after washing. In some embodiments, a biological samples stained by the methods of the invention are stored for later visualization. In general, visualization involves detecting the presence and optionally level of one or more dyes used to stain one or more biological targets in a biological sample, which in turn is indicative of the presence and optionally level of the one or more biological targets in a biological sample. Where the dye is fluorescent dye, visualization may comprise exposure to an excitation frequency, following by detecting frequency and/or intensity of fluorescent light emitted by one or more dyes used to stain a biological sample. In general, the wavelength of excitation for a given dye is shorter than the wavelength emitted by the dye. In some embodiments, the excitation wavelength is about, less than about, or more than about 250 nm, 300 nm, 350 nm, 400 nm, 450 nm, 500 nm, 550 nm, 560 nm, 570 nm, 580 nm, 590 nm, 600 nm, 610 nm, 615, 620 nm, 625, 630 nm, 635, 640 nm, 645, 650 nm, 655, 660 nm, 665, 670 nm, 675, 680 nm, 685, 690 nm, 695, 700 nm, 705, 710 nm, 715, 720 nm, 725, 730 nm, 735, 740 nm, 745, 750 nm, 755, 760 nm, 765, 770 nm, 775, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1020 nm, 1040 nm, 1060 nm, 1080 nm, 1100 nm, 1120 nm, 1140 nm, 1160 nm, 1180 nm, 1200 nm, or any range including two such wavelengths as endpoints, such as from about 350 nm to about 1200 nm, and from about 450 nm to about 750 nm. In some embodiments, the emission wavelength is about, less than about, or more than about 250 nm, 300 nm, 350 nm, 400 nm, 450 nm, 500 nm, 550 nm, 560 nm, 570 nm, 580 nm, 590 nm, 600 nm, 610 nm, 615, 620 nm, 625, 630 nm, 635, 640 nm, 645, 650 nm, 655, 660 nm, 665, 670 nm, 675, 680 nm, 685, 690 nm, 695, 700 nm, 705, 710 nm, 715, 720 nm, 725, 730 nm, 735, 740 nm, 745, 750 nm, 755, 760 nm, 765, 770 nm, 775, 780 nm, 790 nm, 800 nm, 810 nm, 820 nm, 830 nm, 840 nm, 850 nm, 860 nm, 870 nm, 880 nm, 890 nm, 900 nm, 910 nm, 920 nm, 930 nm, 940 nm, 950 nm, 960 nm, 970 nm, 980 nm, 990 nm, 1000 nm, 1020 nm, 1040 nm, 1060 nm, 1080 nm, 1100 nm, 1120 nm, 1140 nm, 1160 nm, 1180 nm, 1200 nm, 1220 nm, 1240 nm, 1250 nm, or any range including two such wavelengths as endpoints, such as from about 360 nm to about 1250 nm.

In some embodiments, a diagnosis of a condition in a subject is made based on the results of the staining process. Conditions that may be diagnosed according to these methods include any that are associated with a detectable marker or characteristic that can be detected by exposure to a labeled protein of the present invention. For example, a large number of antibodies against various disease targets, including but not limited to tumor-associated antigens, have been deposited at the American Type Culture Collection (ATCC) and/or have published variable region sequences and are available for use in the claimed methods and compositions. Antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Examples of diseases and conditions that may be identified using the methods and compositions of the invention include, but are not limited to, inherited diseases, infectious diseases, diseases arising from genetic mutation, poisoning, and cancer.

Labeled proteins of the invention may be used as part of FRET pairs in a variety of biological assays and methods, whether as donor or acceptor molecules. A person skilled in the art will know to select a suitable FRET partner based on the specific application. Such applications include, but are not limited to, assays involving flow cytometry, and any other applications where the relative spatial localization of two or more moieties must be probed. FRET is generally useful on scales of 10 to 100 Å. In one embodiment, both the donor and the acceptor of a FRET pair are labeled molecules of the invention.

The signals produced by the fluorescently labeled proteins of the invention may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 1200 nm, or more commonly from about 350 nm to about 900 nm. Alternatively, compounds of the invention may be excited using an excitation wavelength of about 300 to about 350 nm, 350 to 400 nm, 400 to 450 nm, 450 to 500 nm, 500 to 550 nm, 550 to 600 nm, 600 to 650 nm, 650 to 700 nm, 750 nm to 800 nm, or from 800 nm to 850 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. See, e.g., U.S. Pat. Nos. 7,292,742, 7,181,122, 7,013,054, 6,917,726, 7,267,673, and 7,170,050. These and other optical components known in the art can be combined and assembled in a variety of ways to effect detection of distinguishable signals.

Fluorescently labeled proteins of the invention are useful in a wide variety of assays. Such assays can be performed to discern specific protein-protein interactions, protein-nucleic acid interaction, interactions between a protein of interest and candidate inhibitors or activators. Candidate inhibitors or activators include but are not limited to antisense oligonucleotides, double stranded RNAs, ribozymes, a ribozyme derivatives, antibodies, liposomes, small molecules, inorganic or organic compounds. The subject assays can also be performed to study enzymatic kinetics, for e.g., drug design, screen and/or optimization and can be performed using the fluorescently labeled proteins in solution or immobilized on a solid substrate.

Of particular interest is a specific interaction between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immunoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

A specific interaction between a labeled protein and an interacting entity is assayed by mixing the two entities under conditions such interaction is suspected to occur. Typically, the interaction is visualized with the aid of an optical device. Where desired, these entities can be placed within an optical confinement (see, e.g., U.S. Pat. Nos. 7,267,673, and 7,170, 050). Where single molecule is to be detected, each optical confinement contains only one target that is being investigated. This can be achieved by diluting a minute amount of target in a large volume of solution, such that deposition over an array of confinements results in a primary distribution, or a majority of confinements will have a single target molecule disposed there. The labeled protein and the interacting entity can be immobilized onto the inner surface of the optical confinement by any of the methods available in the art. Such methods encompass the uses of covalent and noncovalent attachments effected by a variety of binding moieties. The choice of the binding moieties will depend on the nature of the labeled protein and/or the interacting entity. One way to immobilize the labeled protein or the proteinaceous probe involves the use of the streptavidin or avidin/biotin binding pair.

Other protein conjugates that can be prepared according to the invention include those of antibodies, lectins, enzymes, lipoproteins, albumins, avidin, streptavidin, annexins, protein A, protein G, transferrin, apotransferrin, phycobiliproteins and other fluorescent proteins, toxins, growth factors, tubulins, hormones, various receptors and ion channels.

If the antigen to be detected is present in very small amounts, a secondary antibody may be used in order to provide signal amplification. Various secondary antibody isotypes may be labeled. Non-limiting examples of secondary antibody isotypes are Anti-mouse IgG, Anti-mouse IgM, Anti-rabbit IgG, Anti-rat IgG, Anti-rat IgM, Anti-guinea pig IgG, Anti-chicken IgG, Anti-hamster IgG, Anti-human IgG, Anti-human IgM, Anti-goat IgG, Anti-mouse IgG, Anti-rabbit IgG, Anti-rat IgG, Anti-sheep IgG, Anti-goat IgG, Anti-mouse IgG, Anti-human IgG, Anti-rat IgG, Anti-mouse IgG, Anti-human IgG, Anti-rat IgG, Anti-goat IgG, and Anti-rabbit IgG.

Alternatively, Fab fragments may be labeled with the compounds of the invention. Such fragments may be superior to whole antibody conjugates because they lack the Fc region, which would reduce nonspecific interactions with Fc receptor-bearing cell membranes and would allow better penetration into tissues.

Labeled secondary antibodies of the invention may be used in signal amplification kits such as those commercialized by Molecular Probes, Inc. Such kits could each provide two labeled antibodies specific to a primary antibodies, such as a mouse antibody. In one embodiment, a rabbit anti-mouse IgG antibody conjugate of the invention is first used to bind to the mouse-derived primary antibody. The fluorescence is then dramatically enhanced by the addition of a second conjugate of a goat anti-rabbit IgG antibody.

Labeled antibodies prepared according to the invention may be primary antibodies for various applications. While secondary detection methods can provide significant signal amplification, a directly labeled primary antibody often produces lower background fluorescence and less nonspecific binding. Using primary antibodies also allows multiple primary antibodies of the same isotype or derived from the same species to be used in the same experiment when they are directly labeled.

Examples of such primary antibodies include polyclonal antibodies specific for reporter gene products. These include Anti-Green-Fluorescent Protein Antibodies, Anti-Glutathione S-Transferase Antibody, Anti-beta-Glucuronidase Antibody, Anti-beta-Galactosidase Antibody, Monoclonal Antibodies Specific for Epitope Tags, Penta.His Antibody, Anti-HA Antibody and Anti-c-myc Antibody.

Organelle-specific labeled antibodies may also be prepared to label various subcellular organelles and components such as the endoplasmic reticulum, peroxisomes, mitochondria, or cytochrome c. Labeled antibodies may also be specific for proteins in the oxidative phosphorylation system, such as antibodies against cytochrome oxidase (Complex IV) or antibodies against Complexes I, II, III and V, or other mitochondrial proteins such as anti-mitochondrial porin antibodies or anti-pyruvate dehydrogenase antibodies.

In other embodiments, labeled antibodies specific for proliferation markers and cell-cycle control proteins may be prepared. Such antibodies include Anti-Bromodeoxyuridine Antibody (Anti-BrdU Antibody), which may for example be used in TUNEL assays, Anti-Human mRNA-Binding Protein HuR Antibody (Anti-HuR Antibody), Anti-Human Neuronal Protein HuC/HuD Antibody (Anti-Hu Antibody), Anti-cdc6 Peptide Antibody, Anti-CD Antibodies, Antibodies against D Cyclins/Cyclin-Dependent Kinase Inhibitors, and Anti-Phosphoinositide Antibodies.

Some labeled antibodies may be specific for structural cellular proteins. Examples of such antibodies are Anti-alpha-Tubulin Monoclonal Antibody, Anti-Glial Fibrillary Acidic Protein (GFAP) Antibody, Anti-Desmin Antibody, or Anti-Fibronectin Antibody. Additional antibodies suitable for use in the invention include antibodies specific for neuronal proteins such as Anti-Synapsin I Antibody or Anti-NMDA Receptor Antibodies. Other Polyclonal and Monoclonal Antibodies that may be labeled according to the invention include Anti-Human Golgin-97 Antibody, Anti-Human Transferrin Receptor Antibody, Antibodies against Matrix Metalloproteinases and Anti-Bovine Serum Albumin Antibody.

The labeled proteins of the invention may be used in single molecule applications. Removal of ensemble averaging by observing individual molecules of fluorescent group may allow the determination of the mechanism of biological and chemical processes. Such processes may include the translocation of protein motors such as kinesin or myosin, formation, dissolution and translocation of cellular protein complexes and the mechanism of action of DNA or RNA polymerases. In such experiments, the present compounds may be used, for example, to label biomolecules which are attached to a surface such as a microscopy slide or flow chamber. Individual fluorophores may subsequently be observed using total internal reflection fluorescence microscopy.

The labeled proteins of the present invention find use as biosensors in prokaryotic and eukaryotic cells, e.g. as calcium ion indicators, as pH indicators, as phorphorylation indicators, as indicators of other ions including without limiting to magnesium, sodium, potassium, chloride and halides. For example, for detection of calcium ion, proteins containing an EF-hand motif are known to translocate from the cytosol to membranes upon binding to calcium ion. These proteins contain a myristoyl group that is buried within the molecule by hydrophobic interactions with other regions of the protein. Binding of calcium ion induces a conformational change exposing the myristoyl group which then is available for the insertion into the lipid bilayer. Labeling such an EF-hand containing protein with a subject fluorescent dye makes it an indicator of intracellular calcium ion concentration by monitoring the translocation from the cytosol to the plasma membrane. Such monitoring can be performed with the use of an optical detector, e.g., a confocal microscope. EF-hand proteins suitable for use in this system include, but are not limited to: recoverin (1-3), calcineurin B, troponin C, visinin, neurocalcin, calmodulin, parvalbumin, and the like.

For use as a pH indicator, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH of approximately 6.5 they typically locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By conjugating the subject fluorescent dye to hisactophilin, the intracellular distribution of the labeled hisactophilin can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells.

The subject labeled proteins also find use in applications involving the automated screening of arrays of cells by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin.

The subject labeled proteins can be used as second messenger detectors, e.g., by conjugating the subject proteins to specific signaling domains, e.g., calcium binding SH2-, SH3-, PH-, PDZ-domain and etc.

Systems

The invention further provides a computer-readable medium comprising code that, upon execution by one or more processors, implements a method, the method comprising selecting an appropriate labeling kit for labeling a target protein mixed with one or more non-target protein(s) in a mixture, wherein said selection is based on the total amount of the target protein and the non-target protein(s) present in the mixture, such that if X µg of the target protein and Y µg of the one or more non-target protein(s) are present in the mixture, then a kit suitable for labeling (X+Y) µg of total protein is chosen for labeling the target protein in said mixture.

Also provided is a computer implemented method for selecting a kit for labeling a target protein, comprising: (a) providing a list of kits for labeling target protein of a given amount, wherein the target protein is present in a mixture containing one or more non-target protein(s); (b) receiving request from an inquirer to select a kit for labeling the target protein of the given amount; (c) selecting with the aid of a processor that is programmed to select an appropriate labeling kit for labeling the target protein based on the total amount of the target protein and the one or more non-target protein(s) present in the mixture, such that if X µg of the target protein and Y µg of the one or more non-target protein(s) are present in the mixture, then a kit suitable for labeling (X+Y) µg of total protein is chosen for labeling the target protein.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

EXAMPLES

Example 1

CF633 Mix-n-Stain Labeling of GAM with Excess BSA

Antibodies labeled using Mix-n-Stain antibody labeling kits (Biotium, Inc., Hayward, Calif.) in the presence of excess stabilizer protein were compared to antibody labeled without stabilizer protein by cell staining and flow cytometry analysis. Goat anti-mouse IgG and bovine serum albumine (BSA) were mixed together in various ratios, then labeled using CF633 Mix-n-Stain kits. Flow cytometry analysis of Jurkat cells was performed to assess the brightness and non-specific background staining of the Mix-n-

Stain labeled conjugates. Jurkat cells ($10^6$/sample) were stained with 0.25 μg of mouse anti-CD3 primary antibody (BD Pharmingen) or no primary antibody, followed by 1 μg of each CF633 Mix-n-Stain labeled goat anti-mouse conjugate. Fluorescence was analyzed by flow cytometry using a BD FACSCalibur flow cytometer in the FL4 channel.

Goat anti-mouse conjugates labeled in the presence of BSA showed similar staining signal compared to conjugate labeled in the absence of BSA, as long as the total amount of protein in the labeling reaction fell within or close to the range of the kit used for labeling (see FIG. 1). A decrease in staining signal was observed when the total amount of protein in the labeling reaction significantly exceeded the kit range, consistent with under-labeling of IgG due to competition for reactive dye from BSA.

Example 2

CF647 Mix-n-Stain Labeling of Mouse Anti-Transferrin Receptor Antibody or Isotype Control with 10-Fold Excess of BSA or Gelatin, Flow Cytometry Mouse anti-transferrin receptor IgG or mouse IgG isotype control (BD Pharmingen) were labeled using CF647 Mix-n-Stain kits (Biotium) using the standard protocol or modified protocol. In the standard protocol, 5 μg IgG without stabilizer protein was labeled using a 5-20 μg size kit according to the kit protocol. In the modified protocol, 5 μg IgG was mixed with 50 μg (10-fold excess by weight) bovine serum albumin (BSA) or porcine gelatin and labeled using 50-100 μg size Mix-n-Stain kits. The total protein concentration was 0.5 mg/mL for all reactions. Flow cytometry analysis of Jurkat cell staining was performed to assess the brightness and non-specific background staining of the Mix-n-Stain labeled conjugates. Jurkat cells ($10^6$/sample) were stained with 0.5 μg of each labeled conjugate and analyzed by flow cytometry using a BD FACSCAlibur flow cytometer in the FL4 channel.

Figures 2A, 2B:
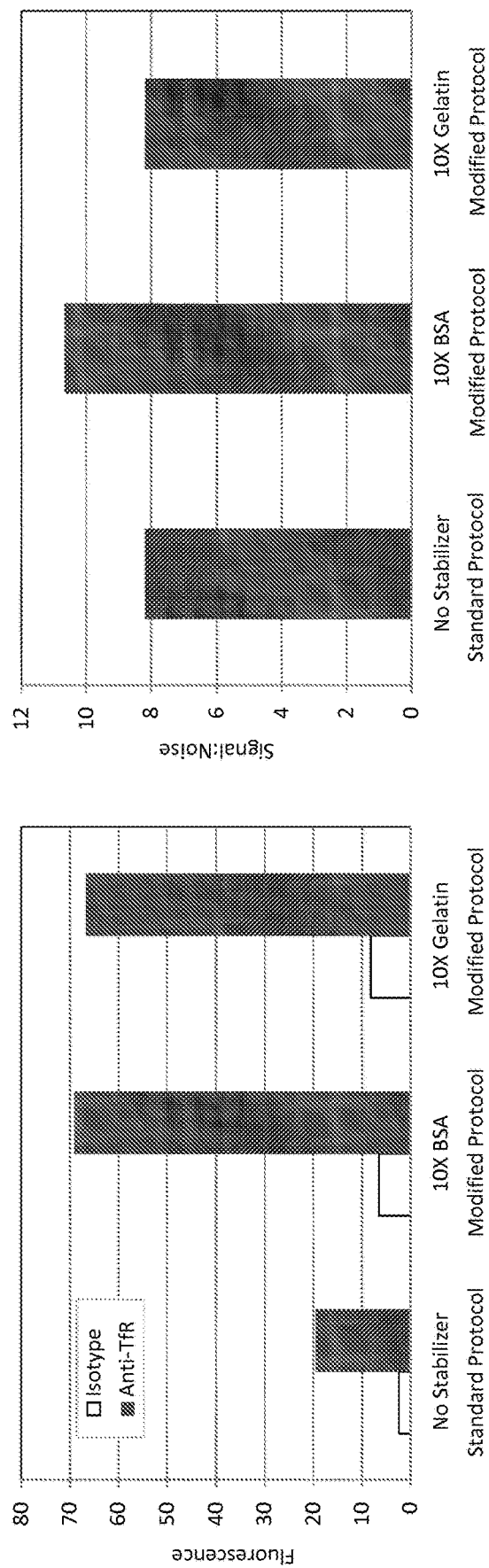
FIG. 2A shows a flow cytometry analysis of Jurkat cells stained with CF647 Mix-n-Stain labeled anti-transferrin receptor IgG (Anti-TfR) or isotype control IgG (Isotype)
FIG. 2B shows signal to noise ratio (Anti-TfR fluorescence/Isotype fluorescence) for the reactions shown in FIG. 2A. IgG labeled in the presence of excess stabilizer protein using the modified Mix-n-Stain labeling method of the invention showed high signal and a similar signal:noise ratio as the standard conjugate.

IgG labeled in the presence of excess stabilizer protein using the modified protocol based on the amount total protein (by weight) rather than amount of IgG in the labeling reaction yielded bright fluorescence signal compared to the standard conjugates (FIG. 2A). While the non-specific background staining of labeled isotype was also higher than the standard conjugate, the conjugates labeled using the modified protocol showed at least similar or higher in some instance signal to noise ratios as the standard conjugates (FIG. 2B).

Example 3

CF647 Mix-n-Stain Labeling of Mouse Anti-Transferrin Receptor Antibody or Isotype Control with 10-Fold Excess of BSA or Gelatin, Fluorescence Microscopy Mix-n-Stain labeling based on total protein amount for antibody labeling in the presence of excess stabilizer protein Mouse anti-transferrin receptor IgG and mouse IgG isotype control from BD Pharmingen were labeled using CF647 Mix-n-Stain kits (Biotium) using the standard protocol or modified protocol. The total protein concentration was adjusted to 0.5 mg/mL for all reactions. In the standard protocol, 5 μg IgG without stabilizer protein was labeled using a 5-20 μg size kit according to the kit protocol. In the modified protocol, 5 μg IgG was mixed with 50 μg (10-fold excess by weight) bovine serum albumin (BSA) or porcine gelatin and labeled using 50-100 μg size kits.

Immunofluorescence staining of HeLa cells was performed to assess antibody specificity after Mix-n-Stain labeling. Intracellular immunofluorescence staining was performed on HeLa cells using 1 μg/mL labeled antibody conjugate, and imaged using a Zeiss LSM 700 confocal microscope. Conjugates labeled in the presence of excess stabilizer protein using the modified Mix-n-Stain protocol showed similar staining patterns as the standard Mix-n-Stain conjugate (see FIG. 3A-C). The plasma membrane and intracellular punctate staining patterns observed were consistent with the localization of transferrin receptor protein, a well-characterized marker for plasma membrane and recycling endosomes.

Example 4

Mix-n-Stain Labeling in the Presence of Excess Stabilizer Protein with PEGylated Dye (CF647) Vs. Non-PEGylated Dye (CF640R)

Mix-n-Stain labeling of IgG in the presence of stabilizer protein results in dye conjugation to both IgG and carrier protein. Blocking agents commonly used in immunostaining protocols should largely prevent non-specific binding of fluorescent carrier protein to samples. In addition, dye modifications that improve water solubility of the dye without introducing an excessive number of charged groups may further reduce non-specific binding of fluorescently labeled stabilizer protein. To test this hypothesis, we compared signal to noise ratio for Mix-n-Stain labeled antibodies using a dye modified with a PEG group to improve water solubility (CF647) versus a non-PEGylated dye (CF640R).

Mouse anti-transferrin receptor IgG or mouse IgG isotype control (BD Pharmingen) were labeled using CF647 or CF640R Mix-n-Stain kits (Biotium) using the standard protocol or modified protocol. The total protein concentration was adjusted to 0.5 mg/mL for all reactions. In the standard protocol, 5 μIgG without stabilizer protein was labeled using a 5-20 μg size kit according to the kit protocol. In the modified protocol, 5 μg IgG was mixed with 50 μg (10-fold excess by weight) bovine serum albumin (BSA) or porcine gelatin and labeled using 50-100 μg size kits.

Figure 4A:
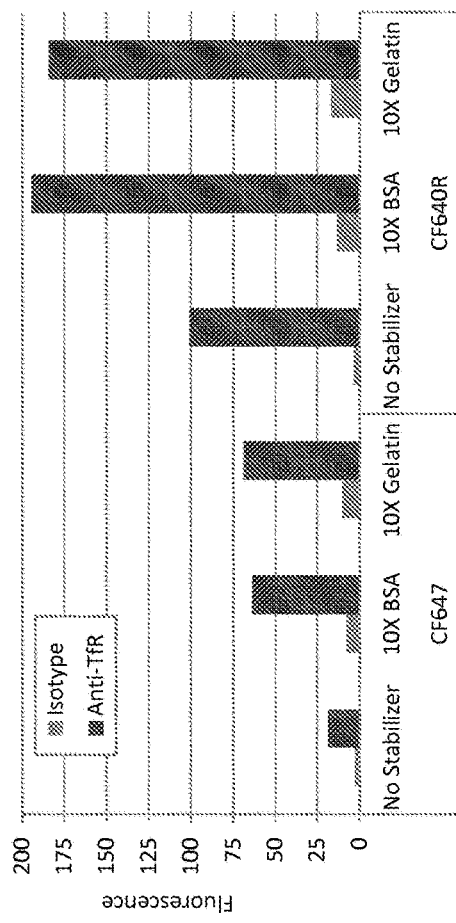
FIG. 4A shows the effect of dye PEGylation on non-specific binding of fluorescently-labeled carrier protein in Mix-n-Stain antibody labeling reactions. The presence of stabilizer protein in Mix-n-Stain labeling reactions increased non-specific background staining compared to Mix-n-Stain reactions with no stabilizer for both PEGylated CF647 dye (Biotium) and non-PEGylated CF640R dye (Biotium). The bars represent geometric mean fluorescence of the cell populations.
Figure 4B:
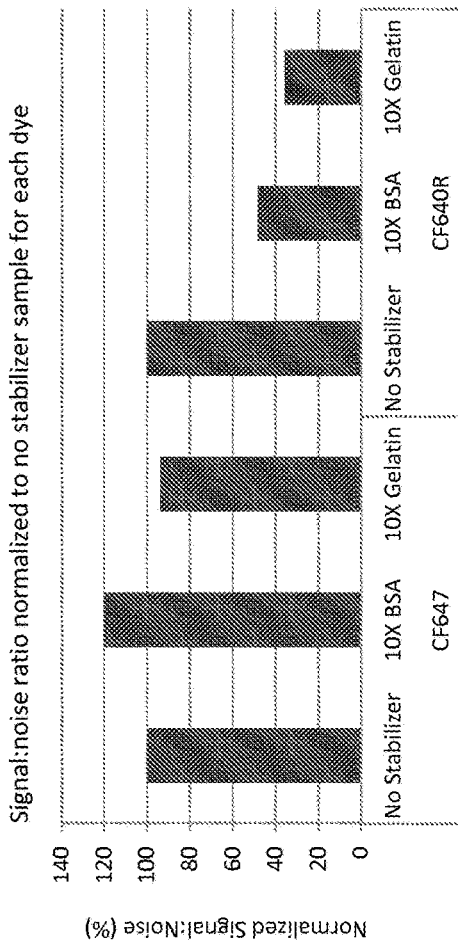
FIG. 4B shows that PEGylated CF647 Mix-n-Stain labeling with excess carrier protein resulted in higher signal to noise ratios compared to non-PEGylated CF640R Mix-n-Stain labeling with excess carrier protein. The bars represent signal to noise ratio, normalized to the signal to noise ratio of the No Stabilizer sample for each dye.
Figure 5A:
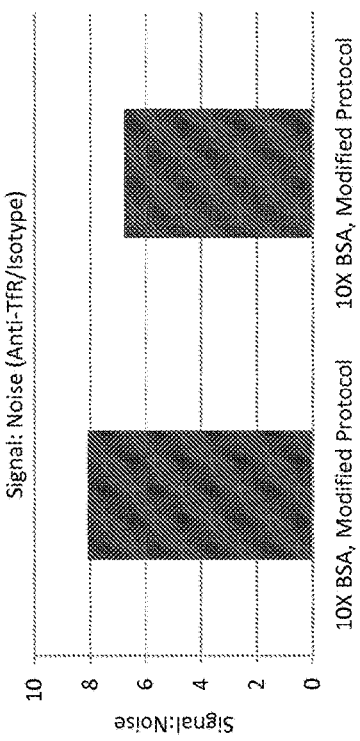
FIG. 5A shows antibody conjugates prepared by a method in accordance of the present invention yielded satisfactory level of florescence even without being concentrated.
Figure 5B:
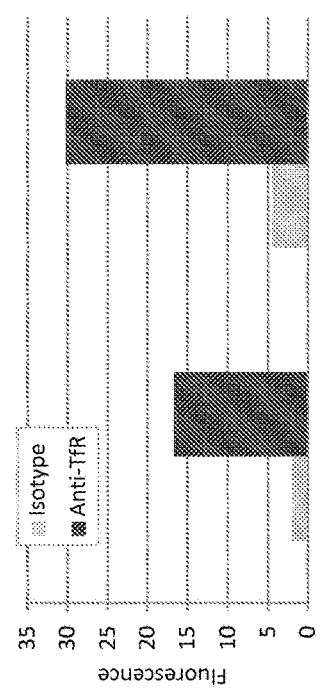
FIG. 5B shows a flow cytometry analysis depicting signal:noise ratio, where both conjugates showed similar fluorescence signal and signal:noise ratios.
Figures 5C, 5D:
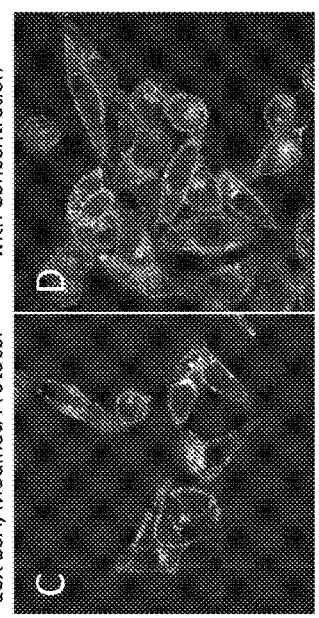
FIG. 5C shows HeLa cell staining with conjugate labeled using a modified Mix-n-Stain labeling method of the invention.
FIG. 5D shows HeLa cells stained with conjugate labeled using a modified Mix-n-Stain labeling method of the invention with concentration by ultrafiltration. Both conjugates showed specific staining patterns typical of transferrin receptor protein localization.
Figure 6:
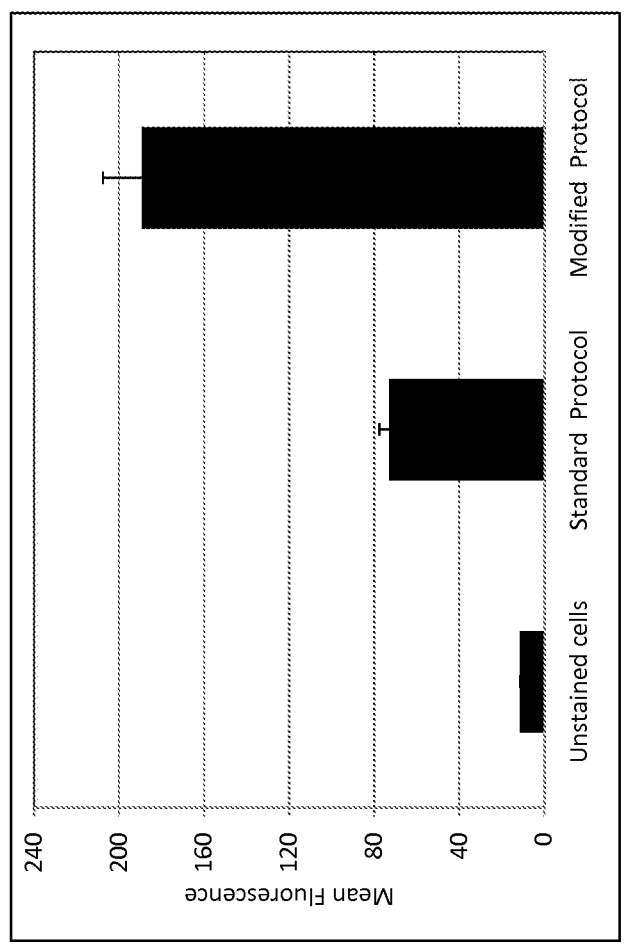
FIG. 6 shows a flow cytometry analysis of Jurkat cells stained with anti-tubulin IgG in ascites fluid. IgG in ascites fluid labeled using a method of the invention showed higher fluorescence signal compared to ascites labeled using a standard protocol.
Figure 10:
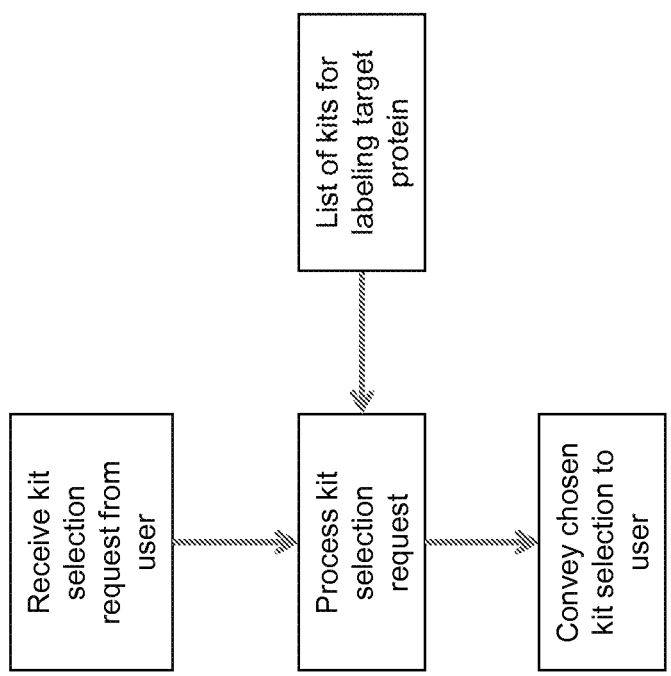
FIG. 10 shows a flow diagram of a computer implemented method of the invention.

Mix-n-Stain labeling in the presence of stabilizer protein increased non-specific background fluorescence of isotype control IgG for both dyes compared to isotype labeled without stabilizer (see FIG. 4A). However, labeling with PEGylated CF647 dye resulted in improved signal to noise ratios compared to labeling with non-PEGylated CF640R (see FIG. 4B), indicating that dye modifications that improve water solubility can reduce non-specific background arising from fluorescently labeled stabilizer protein. Thus, when labeling a target protein in the presence non-target protein, it is preferably to use a PEGylated detectable label.

Example 5

CF647 Mix-n-Stain with Nanosep® Concentration to Exchange Reaction Buffer with Antibody Storage Buffer In the standard Mix-n-Stain labeling protocol, an excess volume of antibody storage buffer is added to the reaction after labeling to neutralize the pH of the labeling solution and introduce antibody stabilizers. However, adding excess storage buffer to the modified Mix-n-Stain labeling reaction results in a very dilute solution of IgG that is not practical to use for subsequent staining steps. Therefore, we tested whether ultrafiltration could be used to rapidly concentrate the labeled IgG prior to adding storage buffer. CF647 Mix-n-Stain labeling was performed in the presence of excess stabilizer protein using the modified Mix-n-Stain protocol. 5 µg IgG was mixed with 50 µg (10-fold excess by weight) bovine serum albumin (BSA) and labeled using a 50-100 µg size kit. In the modified protocol with concentration, the reaction was centrifuged through a microcentrifuge ultrafiltration device with a molecular weight cutoff of 10 kDa (Pall), and the retentate was resuspended in storage buffer at a final concentration of 0.1 mg/mL IgG.

The labeled conjugates were evaluated by flow cytometry analysis of Jurkat cell staining and immunofluorescence staining of HeLa cells. Conjugate labeled using the modified protocol with concentration performed similarly compared to the antibody conjugate labeled using the modified protocol without concentration in flow cytometry and immunofluorescence microscopy assays (see FIG. 5A-D). Therefore ultrafiltration can be used to simply and rapidly exchange reaction buffer for antibody storage buffer for long term storage of antibody conjugates.

Example 6

Mix-n-Stain Labeling of IgG in Ascites Fluid

Antibodies are frequently supplied in unpurified form in crude protein mixtures such as serum, hybridoma cell culture supernatant, or ascites fluid. Purification of IgG is time consuming and can result in reduced antibody affinity; therefore, the ability to conjugate antibodies to dyes in crude preparations would represent a significant advantage over traditional antibody purification and labeling methods.

In order to test whether unpurified IgG in crude protein mixtures could be labeled using Mix-n-Stain antibody labeling kits (Biotium), we labeled mouse anti-tubulin antibody clone DM1A supplied in ascites fluid (Sigma). IgG concentration was reported by manufacturer, and the total protein concentration of the ascites fluid was estimated by measuring absorbance at 280 nm. 5 µg of IgG in ascites fluid (20 µg total protein) was labeled using CF488A Mix-n-Stain using a 5-20 µg kit according to the standard protocol, or using a 50-100 µg kit using the modified protocol.

The brightness of Mix-n-Stain labeled conjugates was evaluated by intracellular immuofluorescence staining of Jurkat cells with 0.5 µg of conjugate compared to unstained cells. Anti-tubulin in ascites fluid labeled using the modified protocol gave brighter signal compared to ascites fluid labeled with the standard protocol indicating that using a larger size results in a higher degree of IgG labeling (see FIG. 6).

The specificity of Mix-n-Stain labeled conjugates was evaluated by intracellular immunofluorescence staining of methanol fixed HeLa cells with 1 µg/mL IgG, compared to cells stained with 1 µg/mL unlabeled IgG in ascites fluid followed by 1 µg/mL CF488A goat anti-mouse secondary antibody conjugate. Direct staining with Mix-n-Stain labeled tubulin resulted in lower fluorescence signal compared to indirect labeling, due to the signal amplification that occurs with secondary antibody detection, therefore FIG. 7B and FIG. 7C were imaged at a higher gain than FIG. 7A. However, HeLa cells stained with Mix-n-Stain labeled anti-tubulin ascites fluid using both the standard and modified protocols showed fluorescence staining (see FIG. 7A-C). However, ascites fluid labeled using the modified protocol yielded higher signal and more specific staining localization (see FIG. 7C) compared to ascites fluid labeled using the standard protocol (see FIG. 7B), showing the advantage of using the modified Mix-n-Stain labeling protocol for labeling of unpurified IgG in ascites fluid.

Example 7

Antibody Labeling with Other Commercial Dyes and Modified Protocol of the Invention To test whether the modified Mix-n-Stain labeling protocol could be applied to dyes or rapid labeling kits from different manufacturers, mouse anti-transferrin receptor IgG was labeled in the presence or absence of excess BSA using the CF488A Mix-n-Stain kit (Biotium), DyLight 488 Lightning Link Rapid kit (Innova Biosciences), or AlexaFluor 488 succinimidyl ester (SE) (Invitrogen) using the standard protocol or modified protocol. The total protein concentration was adjusted to 0.5 mg/mL for all reactions. For Mix-n-Stain standard labeling, 5 µg IgG without stabilizer protein was labeled using a 5-20 µg size kit according to the kit protocol. In the modified protocol, 5 µg IgG was mixed with 50 µg (10-fold excess by weight) bovine serum albumin (BSA) and labeled using a 50-100 µg size kit using the modified Mix-n-Stain protocol. For AlexaFluor SE labeling, the Mix-n-Stain reagents and protocols were used, substituting the same molar amount of AlexaFluor SE dye for CF488 Mix-n-Stain reactive dye. For Dylight 488 Lightning Link Rapid standard labeling, the antibody was labeled according to the manufacturer's protocol. For the Dylight 488 Lightning Link Rapid modified protocol, the amount of protein/antibody added to the reaction was adjusted so that the total protein amount fell within the manufacturer's kit specification.

The labeled conjugates were evaluated by staining HeLa cells with 1 µg/mL conjugate (see FIG. 8A-I). Labeling with the standard protocol without stabilizer protein provided the brightest signal and showed staining patterns typical of transferrin receptor localization (see FIGS. 8A, 8D, and 8G). However, using the modified protocol in the presence of excess stabilizer (see FIGS. 8B, 8E, and 8H) resulted in brighter signal and more specific staining localization compared to labeling with the standard protocol in the presence of excess stabilizer protein (see FIG. 8C, 8F, 8I) for all three dyes (CF488A: A-C; DyLight 488: D-F; AlexaFluor 488: G-I).

Example 8

Mix-n-Stain Labeling of Low Antibody Amounts in the Presence of Excess Stabilizer Protein Using a Protocol of the Invention Mouse anti-transferrin receptor IgG and mouse IgG isotype control from BD Pharmingen were labeled using CF488 AMix-n-Stain kits using the standard protocol or modified protocol. The total protein concentration was adjusted to 0.5 mg/mL for all reactions. In the standard protocol, 5 µg IgG without stabilizer protein was labeled using a 5-20 µg size kit according to the kit protocol. In the modified protocol, IgG was mixed with BSA in 10-fold, 25-fold, or 50-fold excess and labeled using 50-100 µg size kits using the modified protocol.

Immunofluorescence staining of HeLa cells was performed to assess antibody specificity after Mix-n-Stain labeling. Intracellular immunofluorescence staining was performed on HeLa cells using 1 µg/mL labeled antibody conjugate, and imaged using a Zeiss LSM 700 confocal microscope. Conjugates labeled in the presence of excess stabilizer protein using the modified Mix-n-Stain protocol showed similar staining patterns as the standard Mix-n-Stain conjugate (see FIG. 9A-D). The plasma membrane and intracellular punctate staining patterns observed were consistent with the localization of transferrin receptor protein, a well-characterized marker for plasma membrane and recycling endosomes. These results demonstrate that the modified Mix-n-Stain protocol can yield efficient labeling of IgG in the presence of greater than 10-fold excess of stabilizer protein without significantly increasing non-specific background. They also demonstrate that the modified Mix-n-Stain protocol can be used to effectively label small amounts of IgG that fall below the lower limit of a Mix-n-Stain kit by mixing the IgG with BSA to bring the total protein concentration within the range of the kit.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for labeling a target protein, the method comprising:
   (a) providing a reaction mixture comprising the target protein and one or more non-target protein(s), wherein the one or more non-target protein(s) comprise albumin or gelatin, and wherein the ratio of the cumulative weight of the non-target protein to the total weight of the target protein in the reaction mixture is greater than or equal to 1:1 and no more than about 50:1;
   (b) adding to said reaction mixture a reactive label suitable for labeling the target protein;
   (c) stopping the addition of the reactive label to said reaction mixture once an effective amount of the label has been added, wherein the effective amount the label is the sum of:
      (i) an amount of reactive label required for labeling the target protein in the absence of any non-target protein(s) to produce a desired degree of target protein labeling, and
      (ii) an additional amount of reactive label based upon a ratio of a total weight of all non-target protein(s) to a total weight of the target protein; and
   (d) performing a labeling reaction by incubating the reaction mixture and the reactive label in a buffer for less than 2 hours to form a solution of target-label conjugates.

2. The method of claim 1, comprising (d) performing the labeling reaction by incubating the reaction mixture and the reactive label in the buffer for less than 1 hour to form the solution of target-label conjugates.

3. The method of claim 2, comprising (d) performing the labeling reaction by incubating the reaction mixture and the reactive label in the buffer for less than 30 minutes to form the solution of target-label conjugates.

4. The method of claim 1, wherein the ratio of the total weight of the one or more non-target protein(s) to the total weight of the target protein in the reaction mixture is greater than or equal to 20:1.

5. The method of claim 1, wherein the method yields a degree of labeling of the target protein within a range of about 2 to about 20.

6. The method of claim 5, wherein the method yields a degree of labeling of the target protein within a range of about 3 to about 9.

7. The method of claim 1, further comprising adjusting pH of the mixture to neutral pH of about 7 after forming said target-label conjugates.

8. The method of claim 1, wherein the target protein is an antibody.

9. The method of claim 1, further comprising adding one or more preservatives after forming said target-label conjugates.

10. The method of claim 1, further comprising using said target-label conjugates to detect a binding partner of said target.

11. The method of claim 10, wherein said binding partner is an antigen.

12. The method of claim 10, wherein said detecting comprises performing immunostaining.

13. The method of claim 1, wherein the amount of the target protein in the reaction mixture is less than 5 µg.

14. The method of claim 13, wherein the target protein is an antibody.

15. The method of claim 13, further comprising using said target-label conjugates to detect a binding partner of said target.

16. A composition comprising the reaction mixture and the effective amount of the reactive label of claim 1.

17. The composition of claim 16, wherein the target protein is an antibody.

* * * * *